US006296636B1

(12) United States Patent
Cheng et al.

(10) Patent No.: US 6,296,636 B1
(45) Date of Patent: *Oct. 2, 2001

(54) POWER SUPPLY AND METHODS FOR LIMITING POWER IN ELECTROSURGERY

(75) Inventors: Andrew M. L. Cheng, Fremont, CA (US); Philip E. Eggers, Dublin, OH (US); Hira V. Thapliyal, Los Altos, CA (US)

(73) Assignee: ArthroCare Corporation, Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/357,774

(22) Filed: Jul. 21, 1999

Related U.S. Application Data

(60) Division of application No. 09/058,571, filed on Apr. 10, 1998, now Pat. No. 6,142,992, which is a continuation-in-part of application No. 09/010,382, filed on Jan. 21, 1998, now Pat. No. 6,190,381, which is a continuation-in-part of application No. 08/990,374, filed on Dec. 15, 1997, now Pat. No. 6,109,268, which is a continuation-in-part of application No. 08/485,219, filed on Jun. 7, 1995, now Pat. No. 5,697,281, which is a continuation-in-part of application No. PCT/US94/05168, filed on May 10, 1994.
(60) Provisional application No. 60/062,997, filed on Oct. 23, 1997, and provisional application No. 60/075,059, filed on Feb. 18, 1998.

(51) Int. Cl.[7] .................................................. A61B 18/14
(52) U.S. Cl. .............................. 606/32; 606/34; 606/38; 606/41; 606/46; 604/114; 607/99; 607/105; 607/113
(58) Field of Search ........................... 606/32, 34, 37–42, 606/46, 49; 607/99, 105, 113; 604/114

(56) References Cited

U.S. PATENT DOCUMENTS 2,050,904  8/1936  Trice .
4,033,351  7/1977  Hetzel ................................. 128/303
4,040,426  8/1977  Morrison, Jr. ....................... 128/303

(List continued on next page.)

FOREIGN PATENT DOCUMENTS 0 703 461 A2  3/1996  (EP)  .............................. G01R/27/02
0 740 926 A2  11/1996 (EP)  .............................. A61B/17/39
0 754 437     1/1997  (EP)  .............................. A61B/17/39

(List continued on next page.)

OTHER PUBLICATIONS

V.E. Elsasser et al. *Acta Medicotechnica* vol. 24, No. 4, pp. 129–134 (1976).
E.V. Kramolowsky et al. *J. of Urology* vol. 143, pp. 275–277 (1990).
J.W. Ramsey et al. *Urological Research* vol. 13, pp. 99–102 (1985).

(List continued on next page.)

Primary Examiner—Lee Cohen
(74) Attorney, Agent, or Firm—John T. Raffle

(57) ABSTRACT

A high frequency power supply for applying electrical energy to a target site on or within a patient's body includes an electrical output driver, an output current sensor detecting the current output from the driver, and a power limiting device coupled to the current sensor during normal conditions, the power limiting device operates on a continuous basis. When current output exceeds a predetermined threshold level, the power limiting device is adapted to reduce power on the output driver to a standby mode. The power limiting device operates on a periodic detection or duty cycle when in the standby mode. The power limiting device switches into the stand-by mode to prevent excessive power drains. The power supply operates at a low power, pulsatile manner when an attached probe is in conductive or isotonic fluid but is not engaging body tissue or near a high impedance source. In this pulsatile mode, the power supply operates in a cyclical manner, typically at a predetermined duty cycle.

6 Claims, 25 Drawing Sheets

U.S. PATENT DOCUMENTS

| | | | |
|---|---|---|---|
| 4,043,342 | 8/1977 | Morrison, Jr. | 128/303 |
| 4,092,986 | 6/1978 | Schneiderman | 128/303 |
| 4,116,198 | 9/1978 | Roos | 128/303 |
| 4,184,492 | 1/1980 | Meinke et al. | 128/303 |
| 4,188,927 * | 2/1980 | Harris | 606/38 |
| 4,202,337 | 5/1980 | Hren et al. | 128/303 |
| 4,228,800 | 10/1980 | Degler, Jr. et al. | 128/303 |
| 4,232,676 | 11/1980 | Herczog | 128/303 |
| 4,248,231 | 2/1981 | Herczog et al. | 128/303 |
| 4,326,529 | 4/1982 | Doss | 128/303.1 |
| 4,381,007 | 4/1983 | Doss | 228/303.1 |
| 4,476,862 | 10/1984 | Pao | 128/303.17 |
| 4,532,924 | 8/1985 | Auth et al. | 128/303.17 |
| 4,548,207 | 10/1985 | Reimels | 128/303 |
| 4,567,890 | 2/1986 | Ohta et al. | 128/303.13 |
| 4,593,691 | 6/1986 | Lindstrom et al. | 128/303.14 |
| 4,674,499 | 6/1987 | Pao | 128/303 |
| 4,682,596 | 7/1987 | Bales et al. | 128/303 |
| 4,706,667 | 11/1987 | Roos | 128/303 |
| 4,709,698 | 12/1987 | Johnston et al. | 128/303 |
| 4,727,874 | 3/1988 | Bowers et al. | 128/303 |
| 4,765,331 | 8/1988 | Petruzzi et al. | 128/303 |
| 4,823,791 | 4/1989 | D'Amelio et al. | 123/303 |
| 4,860,752 | 8/1989 | Turner | 128/422 |
| 4,931,047 | 6/1990 | Broadwin et al. | 604/22 |
| 4,936,301 | 6/1990 | Rexroth et al. | 606/45 |
| 4,943,290 | 7/1990 | Rexroth et al. | 606/45 |
| 4,955,377 | 9/1990 | Lennox et al. | 128/401 |
| 4,967,765 | 11/1990 | Turner et al. | 128/785 |
| 4,976,711 | 12/1990 | Parins et al. | 606/48 |
| 4,979,948 | 12/1990 | Geddes et al. | 606/33 |
| 4,998,933 | 3/1991 | Eggers et al. | 606/41 |
| 5,007,908 | 4/1991 | Rydell | 606/47 |
| 5,009,656 | 4/1991 | Reimels | 606/48 |
| 5,035,696 | 7/1991 | Rydell | 606/47 |
| 5,057,105 | 10/1991 | Malone et al. | 606/28 |
| 5,057,106 | 10/1991 | Kasevich et al. | 606/33 |
| 5,078,717 | 1/1992 | Parins et al. | 606/48 |
| 5,080,660 | 1/1992 | Buelna | 606/45 |
| 5,083,565 | 1/1992 | Parins | 128/642 |
| 5,098,431 | 3/1992 | Rydell | 606/48 |
| 5,108,391 | 4/1992 | Flachenecker et al. | 606/38 |
| 5,112,330 | 5/1992 | Nishigaki et al. | 606/46 |
| 5,122,138 | 6/1992 | Manwaring | 606/46 |
| 5,125,928 | 6/1992 | Parins et al. | 606/48 |
| 5,178,620 | 1/1993 | Eggers et al. | 606/41 |
| 5,190,517 | 3/1993 | Zieve et al. | 604/22 |
| 5,192,280 | 3/1993 | Parins | 606/48 |
| 5,195,959 | 3/1993 | Smith | 604/34 |
| 5,197,963 | 3/1993 | Parins | 606/46 |
| 5,217,457 | 6/1993 | Delahuerga et al. | 606/42 |
| 5,249,585 | 10/1993 | Turner et al. | 607/99 |
| 5,267,994 | 12/1993 | Gentelia et al. | 606/15 |
| 5,267,997 | 12/1993 | Farin et al. | 606/38 |
| 5,273,524 | 12/1993 | Fox et al. | 604/21 |
| 5,277,201 | 1/1994 | Stern | 607/98 |
| 5,281,216 | 1/1994 | Klicek | 606/42 |
| 5,281,218 | 1/1994 | Imran | 606/41 |
| 5,290,282 | 3/1994 | Casscells | 606/29 |
| 5,300,069 | 4/1994 | Hunsberger et al. | 606/37 |
| 5,312,400 | 5/1994 | Bales et al. | 606/41 |
| 5,314,406 | 5/1994 | Arias et al. | 604/21 |
| 5,318,563 * | 6/1994 | Malis et al. | 606/38 |
| 5,324,254 | 6/1994 | Phillips | 604/21 |
| 5,330,470 | 7/1994 | Hagen | 606/42 |
| 5,334,140 | 8/1994 | Phillips | 604/35 |
| 5,334,183 | 8/1994 | Wuchinich | 606/46 |
| 5,336,220 | 8/1994 | Ryan et al. | 604/22 |
| 5,342,357 | 8/1994 | Nardella | 606/40 |
| 5,366,443 | 11/1994 | Eggers et al. | 606/114 |
| 5,370,675 | 12/1994 | Edwards et al. | 607/101 |
| 5,380,277 | 1/1995 | Phillips | 604/33 |
| 5,383,876 | 1/1995 | Nardella | 606/49 |
| 5,383,917 | 1/1995 | Desai et al. | 607/702 |
| 5,395,312 | 3/1995 | Desai | 604/22 |
| 5,417,687 | 5/1995 | Nardella et al. | 606/32 |
| 5,419,767 | 5/1995 | Eggers et al. | 604/114 |
| 5,441,499 | 8/1995 | Fritzsch | 606/45 |
| 5,454,809 | 10/1995 | Janssen | 606/41 |
| 5,496,312 | 3/1996 | Klicek | 606/34 |
| 5,514,130 | 5/1996 | Baker | 606/41 |
| 5,562,703 | 10/1996 | Desai | 606/21 |
| 5,569,242 | 10/1996 | Lax et al. | 606/42 |
| 5,584,872 | 12/1996 | LaFontaine et al. | 607/116 |
| 5,609,151 | 3/1997 | Mulier et al. | 128/642 |
| 5,628,745 * | 5/1997 | Bek | 606/38 |
| 5,633,578 | 5/1997 | Eggers et al. | 323/301 |
| 5,647,869 | 7/1997 | Goble et al. | 606/37 |
| 5,662,680 | 9/1997 | Desai | 606/210 |
| 5,676,693 | 10/1997 | LaFontaine | 607/116 |
| 5,681,282 | 10/1997 | Eggers et al. | 604/114 |
| 5,683,366 | 11/1997 | Eggers et al. | 604/114 |
| 5,697,281 * | 12/1997 | Eggers et al. | 604/114 |
| 5,697,536 | 12/1997 | Eggers et al. | 604/114 |
| 5,697,882 | 12/1997 | Eggers et al. | 604/114 |
| 5,697,909 | 12/1997 | Eggers et al. | 604/114 |
| 5,700,262 | 12/1997 | Acosta et al. | 606/48 |
| 5,725,524 | 3/1998 | Mulier et al. | 606/41 |
| 5,749,869 | 5/1998 | Lindenmeier et al. | 606/34 |
| 5,766,153 | 6/1998 | Eggers et al. | 604/114 |
| 5,769,847 | 6/1998 | Panescu et al. | 606/42 |
| 5,807,395 | 9/1998 | Mulier et al. | 606/41 |
| 5,810,764 | 9/1998 | Eggers et al. | 604/23 |
| 5,810,802 | 9/1998 | Panescu et al. | 606/31 |
| 5,885,277 | 3/1999 | Korth | 606/35 |
| 5,891,095 | 4/1999 | Eggers et al. | 604/114 |
| 6,004,319 * | 12/1999 | Goble et al. | 606/41 |
| 6,093,186 * | 7/2000 | Goble | 606/34 |

FOREIGN PATENT DOCUMENTS

| | | | |
|---|---|---|---|
| 2 308 979 | 7/1997 | (GB) | |
| 2 308 980 | 7/1997 | (GB) | |
| 2 308 981 | 7/1997 | (GB) | |
| 2327350 | 1/1999 | (GB) | A61B/17/39 |
| 2327351 | 1/1999 | (GB) | A61B/17/39 |
| 2327352 | 1/1999 | (GB) | A61B/17/39 |
| 57-57802 | 4/1982 | (JP) | A61B/1/100 |
| 57-117843 | 7/1982 | (JP) | A61B/17/39 |
| WO 90/07303 | 7/1990 | (WO) | A61B/17/39 |
| WO 92/21278 | 12/1992 | (WO) | A61B/5/04 |
| WO 93/13816 | 7/1993 | (WO) | A61B/17/36 |
| 93/20747 | 10/1993 | (WO) | A61B/5/00 |
| 94/04220 | 3/1994 | (WO) | A61N/1/06 |
| 94/08654 | 4/1994 | (WO) | A61M/37/00 |
| 96/00042 | 1/1996 | (WO) | A61B/17/39 |
| 97/00646 | 1/1997 | (WO) | A61B/17/39 |
| 97/00647 | 1/1997 | (WO) | A61B/17/39 |
| 97/24073 | 7/1997 | (WO) | A61B/17/39 |
| 97/24993 | 7/1997 | (WO) | A61B/17/39 |
| 97/24994 | 7/1997 | (WO) | A61B/17/39 |
| 97/48346 | 12/1997 | (WO) | A61B/17/39 |

OTHER PUBLICATIONS

R. Tucker et al., Abstract P14–11, p. 248, "A Bipolar Electrosurgical Turp Loop".

R. Tucker et al. *J. of Urology* vol. 141, pp. 662–665, (1989).

R. Tucker et al. *Urological Research* vol. 18, pp. 291–294 (1990).

M. Buchelt et al. *Lasers In Surgery and Medecine* 11:271–279 (1991).

J. Costello *Lasers in Surgery and Medecine* 12:121–124 (1992).

P. C. Nardella (1989) *SPIE* 1068:42–49 Radio Frequency Energy and Impedance Feedback.

Rand et al. (1985) *J. Arthro. Surg.* 1:242–246 Effect of Electrocautery on Fresh Human Articular Cartilage.

Pearce, John A. (1986) *Electrosurgery*, pp. 17, 69–75, 87, John Wiley & Sons, New York.

Tucker et al. (1989) Abstract P14–11, $7^{th}$ World Congress on Endourology and ESWL, Nov. 27–30, Kyoto, Japan.

Slager et al. *Z. Kardiol.* 76:Suppl. 6, 67–71 (1987).

* cited by examiner

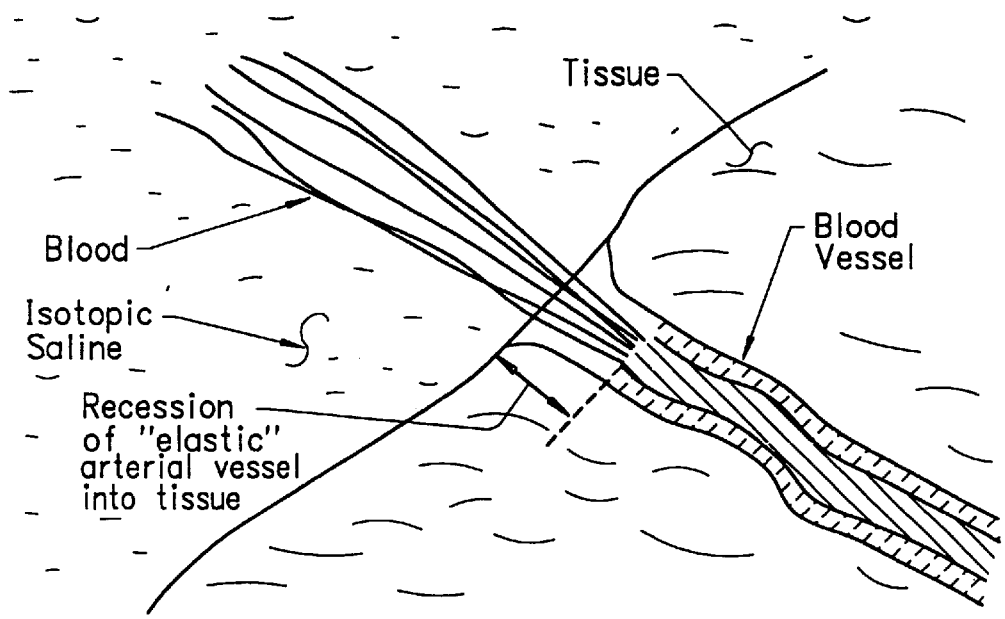
FIG. 1A  ILLUSTRATION OF RETRACTED ARTERIAL BLOOD VESSEL FOLLOWING TRANSECTION
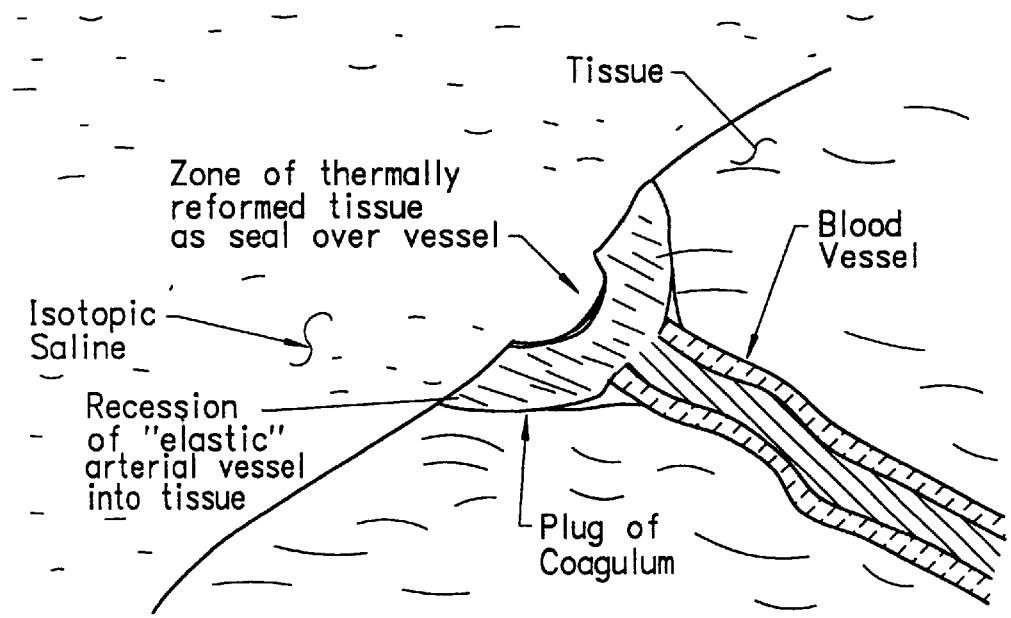
FIG. 1B  ILLUSTRATION OF RETRACTED ARTERIAL BLOOD VESSEL FOLLOWING THERMAL COAGULATION

POWER SUPPLY AND METHODS FOR LIMITING POWER IN ELECTROSURGERY

CROSS REFERENCES TO RELATED APPLICATIONS

This application is a division of application Ser. No. 09/058,571, filed Apr. 10, 1998, now U.S. Pat. No. 6,142,992, an which is a continuation-in-part of and claims priority from co-pending Provisional Patent Application Nos. 60/062,997, filed on Oct. 23, 1997 Ser. No. 60/075,059 filed on Feb. 18, 1998 and non-provisional Patent Application No. 09/010,382, filed Jan. 21, 1998, now U.S. Pat. No. 6,190,381 which is a continuation-in-part of application Ser. No. 08/990,374, filed Dec. 15, 1997, now U.S. Pat. No. 6,109,268, which is a continuation-in-part of application Ser. No. 08/485,219, filed on Jun. 7, 1995, now U.S. Pat. No. 5,697,281, which is a continuation-in-part of PCT International Application, U.S. National Phase Serial No. PCT/US94/05168, filed on May 10, 1994, which was a continuation-in-part of application Ser. No. 08/059,681, filed on May 10, 1993, the complete disclosures of which are incorporated herein by reference for all purposes.

The present invention is also related to commonly assigned U.S. Pat. No. 5,683,366, filed Nov. 22, 1995, U.S. patent application entitled "Systems and Methods for Selective Electrosurgical Treatment of Body Structures", filed Feb. 27, 1998, U.S. patent application Ser. No. 08/977,845, filed on Nov. 25, 1997, Ser. No. 08/942,580, filed on Oct. 2, 1997, application Ser. No. 09/026,851, filed on Feb. 20, 1998, U.S. application Ser. No. 08/753,227, filed on Nov. 22, 1996, U.S. application Ser. No. 08/687,792, filed on Jul. 18, 1996, and U.S. application entitled "Power Supply and Methods for Fluid Delivery in Electrosurgery", filed concurrently with the present application, the complete disclosures of which are incorporated herein by reference for all purposes.

BACKGROUND OF THE INVENTION

The present invention relates generally to the field of electrosurgery and, more particularly, to surgical devices and methods which employ high frequency voltage to treat tissue and other body structures within the body.

The field of electrosurgery includes a number of loosely related surgical techniques which have in common the application of electrical energy to modify the structure or integrity of patient tissue. Electrosurgical procedures usually operate through the application of very high frequency currents to cut or ablate tissue structures, where the operation can be monopolar or bipolar. Monopolar techniques rely on external grounding of the patient, where the surgical device defines only a single electrode pole. Bipolar devices comprise both electrodes for the application of current between their surfaces.

Electrosurgical procedures and techniques are particularly advantageous since they generally reduce patient bleeding and trauma associated with cutting operations. Current electrosurgical device and procedures, however, suffer from a number of disadvantages. For example, conventional electrosurgical cutting devices typically operate by creating a voltage difference between the active electrode and the target tissue, causing an electrical arc to form across the physical gap between the electrode and tissue. At the point of contact of the electric arcs with tissue, rapid tissue heating occurs due to high current density between the electrode and tissue. This high current density causes cellular fluids to rapidly vaporize into steam, thereby producing a "cutting effect" along the pathway of localized tissue heating. Thus, the tissue is parted along the pathway of evaporated cellular fluid, inducing undesirable collateral tissue damage in regions surrounding the target tissue site.

Further, monopolar devices generally direct electric current along a defined path from the exposed or active electrode through the patient's body to the return electrode, which is externally attached to a suitable location on the patient. This creates the potential danger that the electric current will flow through undefined paths in the patient's body, thereby increasing the risk of unwanted electrical stimulation to portions of the patient's body. In addition, since the defined path through the patient's body has a relatively high impedance (because of the large distance or resistivity of the patient's body), large voltage differences must typically be applied between the return and active electrodes in order to generate a current suitable for ablation or cutting of the target tissue. This current, however, may inadvertently flow along body paths having less impedance than the defined electrical path, which will substantially increase the current flowing through these paths, possibly causing damage to or destroying tissue along and surrounding this pathway.

Bipolar electrosurgical devices have an inherent advantage over monopolar devices because the return current path does not flow through the patient. In bipolar electrosurgical devices, both the active and return electrode are typically exposed so that they may both contact tissue, thereby providing a return current path from the active to the return electrode through the tissue. One drawback with this configuration, however, is that the return electrode may cause tissue desiccation or destruction at its contact point with the patient's tissue. In addition, the active and return electrodes are typically positioned close together to ensure that the return current flows directly from the active to the return electrode. The close proximity of these electrodes generates the danger that the current will short across the electrodes, possibly impairing the electrical control system and/or damaging or destroying surrounding tissue.

The use of electrosurgical procedures (both monopolar and bipolar) in electrically conductive environments can be further problematic. For example, many arthroscopic procedures require flushing of the region to be treated with isotonic saline (also referred to as normal saline), both to maintain an isotonic environment and to keep the field of viewing clear. The presence of saline, which is a highly conductive electrolyte, can also cause shorting of the electrosurgical electrode in both monopolar and bipolar modes. Such shorting causes unnecessary heating in the treatment environment and can further cause non-specific tissue destruction.

To overcome the above problems with conventional electrosurgery, improved electrosurgical techniques have been developed using a cold ablation process that employs molecular dissociation or disintegration (rather than thermal evaporation or carbonization) to volumetrically remove body tissue. In these techniques, high frequency voltage is applied to one or more electrode terminal(s) to vaporize an electrically conductive fluid (e.g., gel or isotonic saline) between the electrode terminal(s) and the soft tissue. Within the vaporized fluid, a ionized plasma is formed and charged particles (e.g., electrons) are accelerated towards the tissue to cause the molecular breakdown or disintegration of several cell layers of the tissue. This molecular dissociation is accompanied by the volumetric removal of the tissue. The short range of the accelerated charged particles within the plasma layer confines the molecular dissociation process to the surface layer to minimize damage and necrosis to the underlying tissue. This process can be precisely controlled to effect the volumetric removal of tissue as thin as 10 to 150 microns with minimal heating of, or damage to, surrounding or underlying tissue structures. A more complete description of this phenomena is described in commonly assigned U.S. Pat. No. 5,683,366, the complete disclosure of which is incorporated herein by reference.

This new technology for the electrosurgical removal and/or modification of tissue has, of course, created many new challenges. One such challenge involves excessive power dissipation into the electrically conductive environment surrounding the electrode terminal(s). To perform the above cold ablation technique, conductive fluid is typically either directed to the electrode terminal on the probe (dry fields, such as skin resurfacing) or the conductive fluid is present at the target site during operation (wet fields, such as arthroscopy). When the RF probe is not directly engaging body tissue but still immersed in conductive fluid, relatively large amounts of current may flow from the electrode terminate into the conductive environment. This excessive power wastes energy from the power supply, and may cause it to overheat, which degrades power supply performance and may cause unwanted collateral tissue damage.

Another challenge in electrosurgical procedures involves soft tissue removal in confined spaces where accidental contact is likely to occur between an electrode on the surgical instrument and a low impedance object, such as a metallic endoscope or an anchor. Arthroscopic procedures, laproscopic procedures, and the like are often conducted in confined areas such as the synovial sac of the knee or similar body enclosures. Several instruments, such as an endoscope for visualization and one or two cannulas for surgical access, are often required to perform such surgeries. In arthroscopic procedures, it may also be necessary to remove soft tissue close to an anchor without delivering electrical energy to the anchor. The low impedance of a metallic anchor or the shaft of an endoscope, as compared to the impedance of the surrounding body tissue, may cause a spark or excessive pulse/power drawdown from the instrument. The spark may cause undesired tissue necrosis and also permanently damage surgical equipment such as the endoscope. Delivering current through a metal fastener or anchor may also damage tissue at locations away from the surgical site.

SUMMARY OF THE INVENTION

The present invention is directed to systems, apparatus and methods for ablation, resection, contraction, vaporization and coagulation of tissue. In particular, the present invention is directed to methods and apparatus for limiting the amount of power delivered during electrosurgery, and/or for limiting overcurrents or sparks that may occur when an electrosurgical instrument contacts low impedance objects, such as a metallic endoscope.

In one aspect of the present invention, a high frequency power supply includes an electrical output driver, an output current sensor for detecting the current output from the driver, and a power limiting device coupled to the current sensor. The power supply is configured for use with an electrosurgical probe having a shaft with one or more electrode terminal(s) at the distal end of the shaft. The power supply will be coupled to the electrode terminal(s) and to one or more return electrode(s) for applying a high frequency voltage difference therebetween. Preferably, during normal conditions, the power limiting device operates on a continuous basis. When current output exceeds a predetermined threshold level, the power limiting device is adapted to reduce power on the output driver to a standby mode. The power limiting device operates on a periodic detection or duty cycle when in the standby mode. The power limiting device preferably switches into the stand-by mode to prevent excessive power drains. Preferably, the power supply operates at a low power, pulsatile manner when an attached probe is in conductive or isotonic fluid, but is not engaging body tissue or near a high impedance source. In this pulsatile mode, the power supply operates in a cyclical manner, typically at a predetermined duty cycle.

In one embodiment, the power limiting device senses for changes in output current. Once tissue or other material is engaged by the electrode terminal(s), output current will drop and the power supply will increase current to the probe. In a preferred embodiment, the power supply has a duty cycle of about 100 ms, and includes a logic circuit, such as a Field Programmable Gate Array (FPGA), for determining if the output current is above the preset level. The FPGA's duty cycle is about 10–15 ms on, preferably about 12 ms on, and about 85–90 ms off, preferably about 88 ms off. The power supply usually comprises one or more output current sensors coupled to one or more electrodes on the surgical instrument to determine current output from the power supply. In an exemplary embodiment, the surgical instrument will include a plurality of electrically isolated electrode terminals at the distal end portion of the instrument, and a plurality of independent current sensors coupled to the electrode terminals for selectively limiting power to each of the electrode terminals.

In another aspect of the invention, the power supply includes a spark prevention device for eliminating or reducing sudden pulses in current when an instrument powered by the power supply contacts a low impedance source, such as a metallic endoscope or a metallic fastener, such as an anchor in a patient's knee. The spark limiting device of the power supply is coupled to one or more current sensors on the electrode terminal(s). The spark limiting device substantially continuously monitors current outputs interrupting current output from the output driver when current output from the output current sensor exceeds a predetermined threshold level. The spark prevention mechanism, which may be used in conjunction with the power limiting device, preferably turns off output from the power supply when output current from the supply exceeds a predetermined current level. The spark prevention mechanism operates at a much faster response time and can reduce the power supply output before the power limiting mechanism. In one embodiment, the spark prevention mechanism will shut off output power if output current exceeds between about 1.0–3.0 amps. Typically, attached surgical instruments draw about 0.2 amps. The spark prevention mechanism usually includes a current sensor coupled to an output electrode, a signal conditioner, a voltage comparator, a logic device, and a power output. These elements preferably form a feedback loop. In a preferred embodiment, the spark prevention mechanism and the power limiting mechanism comprise two feedback loops arranged in a serial configuration.

In another aspect of the invention, a system of the present invention includes a high frequency power supply and an electrosurgical instrument coupled to the power supply having one or more electrode terminal(s) on the distal end of the instrument. The system will further include a return electrode, either located on the instrument proximal to the electrode terminal, or as a dispersive pad attached to the patient's skin. According to the invention, the instrument comprises a resistor defining a resistor value for identification purposes, and the system further includes a probe identification device for recognizing the resistor value for the probe. The identification device detects the voltage change created by each resistor. Preferably, the identification device is capable of recognizing at least 8 resistor values.

In an exemplary embodiment, the power supply also includes a switching power supply to increase the peak power output of the generator. The architecture of the switching power supply includes a zero voltage switching topology which minimizes the electromagnetic noise output of the power supply during surgical procedures, thereby ensuring that US and foreign EMI requirements are met. The switching power supply has circuitry which only allows the supply to activate on the zero voltage position of a sinusoidal wave form of AC current.

According to the present invention, a method for applying electrical energy to a target site on or within a patient's body comprises positioning an electrode terminal in contact with or close proximity to tissue at the target site on or within a patient's body. The electrode terminal is coupled to a high frequency power supply and applies high frequency voltage to the electrode terminal to at least modify the tissue. The current output from the power supply is detected and power applied to the electrode terminal is reduced when the current output exceeds a predetermined threshold current. For power limiting, the output from the power supply is reduced to a standby mode. For spark limiting, the output from the power supply is preferably completely stopped. Typically, the signal from a current sensor is conditioned and compared to a value of a predetermined threshold current. For power limiting, the current threshold is usually about 5.0 amperes for power limiting. For spark limiting, the predetermined threshold current is usually about 1.0 to 3.0 amperes.

BRIEF DESCRIPTION OF THE DRAWINGS

FIG. 1A illustrates a retracted arterial blood vessel following transection;

FIG. 1B illustrates a retracted arterial blood vessel following thermal coagulation;

DESCRIPTION OF THE PREFERRED EMBODIMENT

I. Overview

Figure 2:
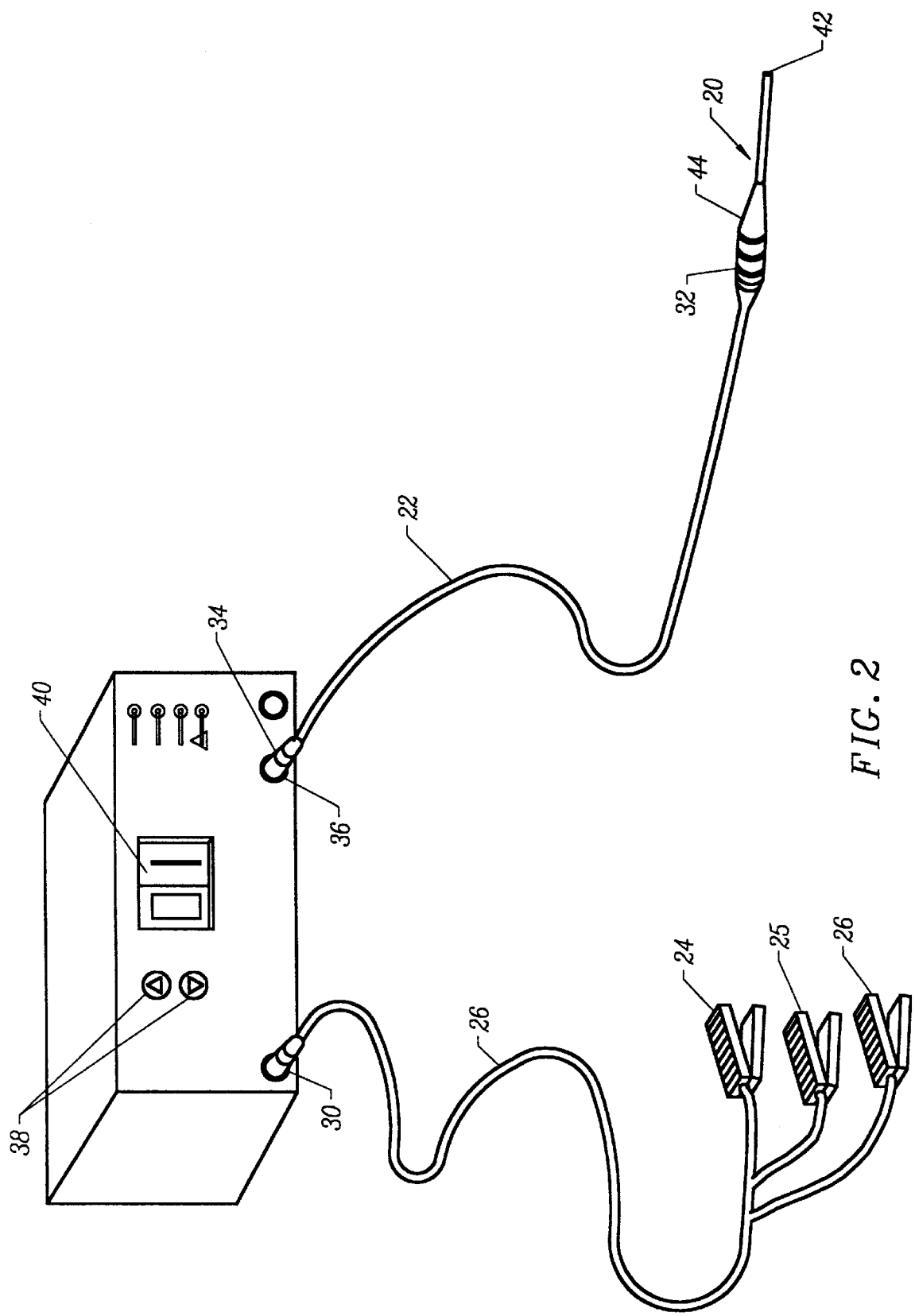
FIG. 2 is a perspective view of a representative electrosurgical system incorporating a power supply according to the present invention and an electrosurgical probe.

The present invention is useful in procedures where the tissue site is flooded or submerged with an electrically conducting fluid, such as arthroscopic surgery of the knee, shoulder, ankle, hip, elbow, hand or foot. Specifically, the present invention is useful in the resection and/or ablation of the meniscus and the synovial tissue within a joint during an arthroscopic procedure. In addition, tissues which may be treated by the system and method of the present invention include, but are not limited to, prostate tissue and leiomyomas (fibroids) located within the uterus, gingival tissues and mucosal tissues located in the mouth, tumors, scar tissue, myocardial tissue, collagenous tissue within the eye or epidermal and dermal tissues on the surface of the skin. The present invention is also useful for resecting tissue within accessible sites of the body that are suitable for electrode loop resection, such as the resection of prostate tissue, leiomyomas (fibroids) located within the uterus and other diseased tissue within the body.

The present invention is particularly useful for treating tissue in the head and neck, such as the ear, mouth, pharynx, larynx, esophagus, nasal cavity and sinuses. The head and neck procedures may be performed through the mouth or nose using speculae or gags, or using endoscopic techniques, such as functional endoscopic sinus surgery (FESS). These procedures may include the removal of swollen tissue, chronically-diseased inflamed and hypertrophic mucus linings, polyps, turbinates and/or neoplasms from the various anatomical sinuses of the skull, the turbinates and nasal passages, in the tonsil, adenoid, epi-glottic and supra-glottic regions, and salivary glands, submucus resection of the nasal septum, excision of diseased tissue and the like. In other procedures, the present invention may be useful for collagen shrinkage, ablation and/or hemostasis in procedures for treating swollen tissue (e.g., turbinates) or snoring and obstructive sleep apnea (e.g., soft palate, such as the uvula, or tongue/pharynx stiffening, and midline glossectomies), for gross tissue removal, such as tonsillectomies, adenoidectomies, tracheal stenosis and vocal cord polyps and lesions, or for the resection or ablation of facial tumors or tumors within the mouth and pharynx, such as glossectomies, laryngectomies, acoustic neuroma procedures and nasal ablation procedures. In addition, the present invention is useful for procedures within the ear, such as stapedotomies, tympanostomies or the like.

The present invention may also be useful for treating tissue or other body structures in the brain or spine. These procedures include tumor removal, laminectomy/disketomy procedures for treating herniated disks, decompressive larninectomy for stenosis in the lumbosacral and cervical spine, medial facetectomy, posterior lumbosacral and cervical spine fusions, treatment of scoliosis associated with vertebral disease, foraminotomies to remove the roof of the intervertebral foramina to relieve nerve root compression and anterior cervical and lumbar diskectomies. These procedures may be performed through open procedures, or using minimally invasive techniques, such as thoracoscopy, arthroscopy, laparascopy or the like.

The present invention may also be useful for cosmetic and plastic surgery procedures in the head and neck. For example, the present invention is particularly useful for ablation and sculpting of cartilage tissue, such as the cartilage within the nose that is sculpted during rhinoplasty procedures. The present invention may also be employed for skin tissue removal and/or collagen shrinkage in the epidermis or dermis tissue in the head and neck, e.g., the removal of pigmentations, vascular lesions (e.g., leg veins), scars, tattoos, etc., and for other surgical procedures on the skin, such as tissue rejuvenation, cosmetic eye procedures (blepharoplasties), wrinkle removal, tightening muscles for facelifts or browlifts, hair removal and/or transplant procedures, etc.

For convenience, the remaining disclosure will be directed specifically to the treatment of tissue structures within a joint, e.g., arthroscopic surgery, but it will be appreciated that the system and method can be applied equally well to procedures involving other tissues of the body, as well as to other procedures including open procedures, intravascular procedures, urology, laparascopy, arthroscopy, thoracoscopy or other cardiac procedures, cosmetic surgery, orthopedics, gynecology, otorhinolaryngology, spinal and neurologic procedures, oncology and the like.

In the present invention, high frequency (RF) electrical energy is applied to one or more electrode terminals in the presence of electrically conductive fluid to remove and/or modify the structure of tissue structures. Depending on the specific procedure, the present invention may be used to: (1) volumetrically remove tissue or cartilage (i.e., ablate or effect molecular dissociation of the tissue structure); (2) cut or resect tissue; (3) shrink or contract collagen connective tissue; and/or (4) coagulate severed blood vessels.

In one method of the present invention, it is desired to operate the invention in a subablation modality to shrink or contract tissue at a target site or to cause blood vessel coagulation. In collagen shrinkage procedures, the RF energy heats the tissue directly by virtue of the electrical current flow therethrough, and/or indirectly through the exposure of the tissue to fluid heated by RF energy, to elevate the tissue temperature from normal body temperatures (e.g., 37° C.) to temperatures in the range of 45° C. to 90° C., preferably in the range from about 60° C. to 70° C. Thermal shrinkage of collagen fibers occurs within a small temperature range which, for mammalian collagen is in the range from 60° C. to 70° C. (Deak, G., et al., "The Thermal Shrinkage Process of Collagen Fibres as Revealed by Polarization Optical Analysis of Topooptical Staining Reactions," Acta Morphologica Acad. Sci. of Hungary, Vol. 15(2), pp 195–208, 1967). Collagen fibers typically undergo thermal shrinkage in the range of 60° C. to about 70° C. Previously reported research has attributed thermal shrinkage of collagen to the cleaving of the internal stabilizing cross-linkages within the collagen matrix (Deak, ibid). It has also been reported that when the collagen temperature is increased above 70° C., the collagen matrix begins to relax again and the shrinkage effect is reversed resulting in no net shrinkage (Allain, J. C., et al., "Isometric Tensions Developed During the Hydrothermal Swelling of Rat Skin," Connective Tissue Research, Vol. 7, pp 127–133, 1980). Consequently, the controlled heating of tissue to a precise depth is critical to the achievement of therapeutic collagen shrinkage. A more detailed description of collagen shrinkage can be found in U.S. patent application Ser. No. 08/942,580, filed on Oct. 2, 1997, (Attorney Docket No. 16238-001300).

In some procedures, the tissue structures are volumetrically removed or ablated by applying a high frequency voltage difference between one or more electrode terminal (s) and one or more return electrode(s). The voltage difference is sufficient to develop high electric field intensities in the vicinity of the target tissue site, which lead to electric field induced molecular breakdown of target tissue through molecular dissociation (rather than thermal evaporation or carbonization). The tissue structure is volumetrically removed through molecular disintegration of larger organic molecules into smaller molecules and/or atoms, such as hydrogen, oxides of carbon, hydrocarbons and nitrogen compounds. This molecular disintegration completely removes the tissue structure, as opposed to dehydrating the tissue material by the removal of liquid within the cells of the tissue, as is typically the case with electrosurgical desiccation and vaporization.

The high electric field intensities may be generated by applying a high frequency voltage that is sufficient to vaporize an electrically conducting fluid over at least a portion of the electrode terminal(s) in the region between the distal tip of the electrode terminal(s) and the target tissue. The electrically conductive fluid may be a gas or liquid, such as isotonic saline, delivered to the target site, or a viscous fluid, such as a gel, that is located at the target site. In the latter embodiment, the electrode terminal(s) are submersed in the electrically conductive gel during the surgical procedure. Since the vapor layer or vaporized region has a relatively high electrical impedance, it increases the voltage differential between the electrode terminal tip and the tissue and causes ionization within the vapor layer due to the presence of an ionizable species (e.g., sodium when isotonic saline is the electrically conducting fluid). This ionization, under optimal conditions, induces the discharge of energetic electrons and photons from the vapor layer and to the surface of the target tissue. This energy may be in the form of energetic photons (e.g., ultraviolet radiation), energetic particles (e.g., electrons) or a combination thereof. A more detailed description of this cold ablation phenomena, termed Coblation™, can be found in commonly assigned U.S. Pat. No. 5,683,366 the complete disclosure of which is incorporated herein by reference.

The present invention applies high frequency (RF) electrical energy in an electrically conducting fluid environment to remove (i.e., resect, cut or ablate) or contract a tissue structure, and to seal transected vessels within the region of the target tissue. The present invention is particularly useful for sealing larger arterial vessels, e.g., on the order of 1 mm or greater. In some embodiments, a high frequency power supply is provided having an ablation mode, wherein a first voltage is applied to an electrode terminal sufficient to effect molecular dissociation or disintegration of the tissue, and a coagulation mode, wherein a second, lower voltage is applied to an electrode terminal (either the same or a different electrode) sufficient to achieve hemostasis of severed vessels within the tissue. In other embodiments, an electrosurgical probe is provided having one or more coagulation electrode(s) configured for sealing a severed vessel, such as an arterial vessel, and one or more electrode terminals configured for either contracting the collagen fibers within the tissue or removing (ablating) the tissue, e.g., by applying sufficient energy to the tissue to effect molecular dissociation. In the latter embodiments, the coagulation electrode(s) may be configured such that a single voltage can be applied to coagulate with the coagulation electrode(s), and to ablate or contract with the electrode terminal(s). In other embodiments, the power supply is combined with the coagulation probe such that the coagulation electrode is used when the power supply is in the coagulation mode (low voltage), and the electrode terminal(s) are used when the power supply is in the ablation mode (higher voltage).

In the method of the present invention, one or more electrode terminals are brought into close proximity to tissue at a target site, and the power supply is activated in the ablation mode such that sufficient voltage is applied between the electrode terminals and the return electrode to volumetrically remove the tissue through molecular dissociation, as described below. During this process, vessels within the tissue will be severed. Smaller vessels will be automatically sealed with the system and method of the present invention. Larger vessels, and those with a higher flow rate, such as arterial vessels, may not be automatically sealed in the ablation mode. In these cases, the severed vessels may be sealed by activating a control (e.g., a foot pedal) to reduce the voltage of the power supply into the coagulation mode. In this mode, the electrode terminals may be pressed against the severed vessel to provide sealing and/or coagulation of the vessel. Alternatively, a coagulation electrode located on the same or a different probe may be pressed against the severed vessel. Once the vessel is adequately sealed, the surgeon activates a control (e.g., another foot pedal) to increase the voltage of the power supply back into the ablation mode.

The present invention is particularly useful for removing or ablating tissue around nerves, such as spinal or cranial nerves, e.g., the olfactory nerve on either side of the nasal cavity, the optic nerve within the optic and cranial canals, the palatine nerve within the nasal cavity, soft palate, uvula and tonsil, etc. One of the significant drawbacks with the prior art microdebriders and lasers is that these devices do not differentiate between the target tissue and the surrounding nerves or bone. Therefore, the surgeon must be extremely careful during these procedures to avoid damage to the bone or nerves within and around the nasal cavity. In the present invention, the Coblation™ process for removing tissue results in extremely small depths of collateral tissue damage as discussed above. This allows the surgeon to remove tissue close to a nerve without causing collateral damage to the nerve fibers.

In addition to the generally precise nature of the novel mechanisms of the present invention, applicant has discovered an additional method of ensuring that adjacent nerves are not damaged during tissue removal. According to the present invention, systems and methods are provided for distinguishing between the fatty tissue immediately surrounding nerve fibers and the normal tissue that is to be removed during the procedure. Nerves usually comprise a connective tissue sheath, or endoneurium, enclosing the bundles of nerve fibers to protect these nerve fibers. This protective tissue sheath typically comprises a fatty tissue (e.g., adipose tissue) having substantially different electrical properties than the normal target tissue, such as the turbinates, polyps, mucus tissue or the like, that are, for example, removed from the nose during sinus procedures. The system of the present invention measures the electrical properties of the tissue at the tip of the probe with one or more electrode terminal(s). These electrical properties may include electrical conductivity at one, several or a range of frequencies (e.g., in the range from 1 kHz to 100 MHz), dielectric constant, capacitance or combinations of these. In this embodiment, an audible signal may be produced when the sensing electrode(s) at the tip of the probe detects the fatty tissue surrounding a nerve, or direct feedback control can be provided to only supply power to the electrode terminal(s) either individually or to the complete array of electrodes, if and when the tissue encountered at the tip or working end of the probe is normal tissue based on the measured electrical properties.

In one embodiment, the current limiting elements (discussed in detail above) are configured such that the electrode terminals will shut down or turn off when the electrical impedance reaches a threshold level. When this threshold level is set to the impedance of the fatty tissue surrounding nerves, the electrode terminals will shut off whenever they come in contact with, or in close proximity to, nerves. Meanwhile, the other electrode terminals, which are in contact with or in close proximity to nasal tissue, will continue to conduct electric current to the return electrode. This selective ablation or removal of lower impedance tissue in combination with the Coblation™ mechanism of the present invention allows the surgeon to precisely remove tissue around nerves or bone.

In addition to the above, applicant has discovered that the Coblation™ mechanism of the present invention can be manipulated to ablate or remove certain tissue structures, while having little effect on other tissue structures. As discussed above, the present invention uses a technique of vaporizing electrically conductive fluid to form a plasma layer or pocket around the electrode terminal(s), and then inducing the discharge of energy from this plasma or vapor layer to break the molecular bonds of the tissue structure. Based on initial experiments, applicants believe that the free electrons within the ionized vapor layer are accelerated in the high electric fields near the electrode tip(s). When the density of the vapor layer (or within a bubble formed in the electrically conducting liquid) becomes sufficiently low (i.e., less than approximately $10^{20}$ atoms/cm$^3$ for aqueous solutions), the electron mean free path increases to enable subsequently injected electrons to cause impact ionization within these regions of low density (i.e., vapor layers or bubbles). Energy evolved by the energetic electrons (e.g., 4 to 5 eV) can subsequently bombard a molecule and break its bonds, dissociating a molecule into free radicals, which then combine into final gaseous or liquid species.

The energy evolved by the energetic electrons may be varied by adjusting a variety of factors, such as: the number of electrode terminals; electrode size and spacing; electrode surface area; asperities and sharp edges on the electrode surfaces; electrode materials; applied voltage and power; current limiting means, such as inductors; electrical conductivity of the fluid in contact with the electrodes; density of the fluid; and other factors. Accordingly, these factors can be manipulated to control the energy level of the excited electrons. Since different tissue structures have different molecular bonds, the present invention can be configured to break the molecular bonds of certain tissue, while having too low an energy to break the molecular bonds of other tissue. For example, fatty tissue, (e.g., adipose) tissue has double bonds that require a substantially higher energy level than 4 to 5 eV to break. Accordingly, the present invention in its current configuration generally does not ablate or remove such fatty tissue. Of course, factors may be changed such that these double bonds can be broken (e.g., increasing voltage or changing the electrode configuration to increase the current density at the electrode tips).

The electrosurgical probe or catheter will comprise a shaft or a handpiece having a proximal end and a distal end which supports one or more electrode terminal(s). The shaft or handpiece may assume a wide variety of configurations, with the primary purpose being to mechanically support the active electrode and permit the treating physician to manipulate the electrode from a proximal end of the shaft. The shaft may be rigid or flexible, with flexible shafts optionally being combined with a generally rigid external tube for mechanical support. Flexible shafts may be combined with pull wires, shape memory actuators, and other known mechanisms for effecting selective deflection of the distal end of the shaft to facilitate positioning of the electrode array. The shaft will usually include a plurality of wires or other conductive elements running axially therethrough to permit connection of the electrode array to a connector at the proximal end of the shaft.

The current flow path between the electrode terminal(s) and the return electrode(s) may be generated by submerging the tissue site in an electrical conducting fluid (e.g., within a viscous fluid, such as an electrically conductive gel) or by directing an electrically conducting fluid along a fluid path to the target site (i.e., a liquid, such as isotonic saline, or a gas, such as argon). This latter method is particularly effective in a dry environment (i.e., the tissue is not submerged in fluid) because the electrically conducting fluid provides a suitable current flow path from the electrode terminal to the return electrode. A more complete description of an exemplary method of directing electrically conducting fluid between the active and return electrodes is described in U.S. Pat. No. 5,697,281, previously incorporated herein by reference.

In some procedures, it may also be necessary to retrieve or aspirate the electrically conductive fluid after it has been directed to the target site. In addition, it may be desirable to aspirate small pieces of tissue that are not completely disintegrated by the high frequency energy, or other fluids at the target site, such as blood, mucus, the gaseous products of ablation, etc. Accordingly, the system of the present invention will usually include a suction lumen in the probe, or on another instrument, for aspirating fluids from the target site. In addition, the invention may include one or more aspiration electrode(s) coupled to the distal end of the suction lumen for ablating, or at least reducing the volume of, non-ablated tissue fragments that are aspirated into the lumen. The aspiration electrode(s) function mainly to inhibit clogging of the lumen that may otherwise occur as larger tissue fragments are drawn therein. The aspiration electrode (s) may be different from the ablation electrode terminal(s), or the same electrode(s) may serve both functions. A more complete description of probes incorporating aspiration electrode(s) can be found in commonly assigned, co-pending patent application Ser. No. 09/010,382, filed on Jan. 21, 1998, the complete disclosure of which is incorporated herein by reference.

The present invention may use a single active electrode terminal or an electrode array distributed over a contact surface of a probe. In the latter embodiment, the electrode array usually includes a plurality of independently current-limited and/or power-controlled electrode terminals to apply electrical energy selectively to the target tissue while limiting the unwanted application of electrical energy to the surrounding tissue and environment resulting from power dissipation into surrounding electrically conductive liquids, such as blood, normal saline, electrically conductive gel and the like. The electrode terminals may be independently current-limited by isolating the terminals from each other and connecting each terminal to a separate power source that is isolated from the other electrode terminals. Alternatively, the electrode terminals may be connected to each other at either the proximal or distal ends of the probe to form a single wire that couples to a power source.

The active electrode(s) are typically mounted in an electrically insulating electrode support that extends from the electrosurgical probe. In some embodiments, the electrode support comprises a plurality of wafer layers bonded together, e.g., by a glass adhesive or the like, or a single wafer. The wafer layer(s) have conductive strips printed thereon to form the electrode terminal(s) and the return electrode(s). In one embodiment, the proximal end of the wafer layer(s) will have a number of holes extending from the conductor strips to an exposed surface of the wafer layers for connection to electrical conductor lead traces in the electrosurgical probe or handpiece. The wafer layers preferably comprise a ceramic material, such as alumina, and the electrode will preferably comprise a metallic material, such as gold, copper, platinum, palladium, tungsten, silver or the like. Suitable multilayer ceramic electrodes are commercially available from e.g., VisPro Corporation of Beaverton, Oreg.

In one configuration, each individual electrode terminal in the electrode array is electrically insulated from all other electrode terminals in the array within said probe and is connected to a power source which is isolated from each of the other electrode terminals in the array or to circuitry which limits or interrupts current flow to the electrode terminal when low resistivity material (e.g., blood, electrically conductive saline irrigant or electrically conductive gel) causes a lower impedance path between the return electrode and the individual electrode terminal. The isolated power sources for each individual electrode terminal may be separate power supply circuits having internal impedance characteristics which limit power to the associated electrode terminal when a low impedance return path is encountered. By way of example, the isolated power source may be a user selectable constant current source. In this embodiment, lower impedance paths will automatically result in lower resistive heating levels since the heating is proportional to the square of the operating current times the impedance. Alternatively, a single power source may be connected to each of the electrode terminals through independently actuatable switches, or by independent current limiting elements, such as inductors, capacitors, resistors and/or combinations thereof. The current limiting elements may be provided in the probe, connectors, cable, controller or along the conductive path from the controller to the distal tip of the probe. Alternatively, the resistance and/or capacitance may occur on the surface of the active electrode terminal(s) due to oxide layers which form selected electrode terminals (e.g., titanium or a resistive coating on the surface of metal, such as platinum).

The tip region of the probe may comprise many independent electrode terminals designed to deliver electrical energy in the vicinity of the tip. The selective application of electrical energy to the conductive fluid is achieved by connecting each individual electrode terminal and the return electrode to a power source having independently controlled or current limited channels. The return electrode(s) may comprise a single tubular member of conductive material proximal to the electrode array at the tip which also serves as a conduit for the supply of the electrically conducting fluid between the active and return electrodes. Alternatively, the probe may comprise an array of return electrodes at the distal tip of the probe (together with the active electrodes) to maintain the electric current at the tip. The application of high frequency voltage between the return electrode(s) and the electrode array results in the generation of high electric field intensities at the distal tips of the electrode terminals with conduction of high frequency current from each individual electrode terminal to the return electrode. The current flow from each individual electrode terminal to the return electrode(s) is controlled by either active or passive means, or a combination thereof, to deliver electrical energy to the surrounding conductive fluid while minimizing energy delivery to surrounding (non-target) tissue.

The application of a high frequency voltage between the return electrode(s) and the electrode terminal(s) for appropriate time intervals effects cutting, removing, ablating, shaping, contracting or otherwise modifying the target tissue. The tissue volume over which energy is dissipated (i.e., a high current density exists) may be precisely controlled, for example, by the use of a multiplicity of small electrode terminals whose effective diameters or principal dimensions range from about 5 mm to 0.01 mm, preferably from about 2 mm to 0.05 mm, and more preferably from about 1 mm to 0.1 mm. Electrode areas for both circular and non-circular terminals will have a contact area (per electrode terminal) below 25 $mm^2$, preferably being in the range from 0.0001 $mm^2$ to 1 $mm^2$, and more preferably from 0.005 $mm^2$ to 0.5 $mm^2$. The circumscribed area of the electrode array is in the range from 0.25 $mm^2$ to 75 $mm^2$, preferably from 0.5 $mm^2$ to 40 $mm^2$, and will usually include at least two isolated electrode terminals, preferably at least five electrode terminals, often greater than 10 electrode terminals and even 50 or more electrode terminals, disposed over the distal contact surfaces on the shaft. The use of small diameter electrode terminals increases the electric field intensity and reduces the extent or depth of tissue heating as a consequence of the divergence of current flux lines which emanate from the exposed surface of each electrode terminal.

The area of the tissue treatment surface can vary widely, and the tissue treatment surface can assume a variety of geometries, with particular areas and geometries being selected for specific applications. Active electrode surfaces can have areas in the range from 0.25 $mm^2$ to 75 $mm^2$, usually being from about 0.5 $mm^2$ to 40 $mm^2$. The geometries can be planar, concave, convex, hemispherical, conical, linear "in-line" array or virtually any other regular or irregular shape. Most commonly, the active electrode(s) or electrode terminal(s) will be formed at the distal tip of the electrosurgical probe shaft, frequently being planar, disk-shaped, or hemispherical surfaces for use in reshaping procedures or being linear arrays for use in cutting. Alternatively or additionally, the active electrode(s) may be formed on lateral surfaces of the electrosurgical probe shaft (e.g., in the manner of a spatula), facilitating access to certain body structures in endoscopic procedures.

In the representative embodiments, the electrode terminals comprise substantially rigid wires protruding outward from the tissue treatment surface of the electrode support member. Usually, the wires will extend about 0.1 to 4.0 mm, preferably about 0.2 to 1 mm, from the distal surface of the support member. In the exemplary embodiments, the electrosurgical probe includes between about two to fifty electrically isolated electrode terminals, and preferably between about three to twenty electrode terminals.

The electrically conducting fluid should have a threshold conductivity to provide a suitable conductive path between the return electrode(s) and the electrode terminal(s). The electrical conductivity of the fluid (in units of milliSiemans per centimeter or mS/cm) will usually be greater than 0.2 mS/cm, preferably will be greater than 2 mS/cm and more preferably greater than 10 mS/cm. In an exemplary embodiment, the electrically conductive fluid is isotonic saline, which has a conductivity of about 17 mS/cm.

In some embodiments, the electrode support and the fluid outlet may be recessed from an outer surface of the probe or handpiece to confine the electrically conductive fluid to the region immediately surrounding the electrode support. In addition, the shaft may be shaped so as to form a cavity around the electrode support and the fluid outlet. This helps to assure that the electrically conductive fluid will remain in contact with the electrode terminal(s) and the return electrode(s) to maintain the conductive path therebetween. In addition, this will help to maintain a vapor or plasma layer between the electrode terminal(s) and the tissue at the treatment site throughout the procedure, which reduces the thermal damage that might otherwise occur if the vapor layer were extinguished due to a lack of conductive fluid. Provision of the electrically conductive fluid around the target site also helps to maintain the tissue temperature at desired levels.

The voltage applied between the return electrode(s) and the electrode array will be at high or radio frequency, typically between about 5 kHz and 20 MHz, usually being between about 30 kHz and 2.5 MHz, preferably being between about 50 kHz and 500 kHz, more preferably less than 350 kHz, and most preferably between about 100 kHz and 200 kHz. The RMS (root mean square) voltage applied will usually be in the range from about 5 volts to 1000 volts, preferably being in the range from about 10 volts to 500 volts depending on the electrode terminal size, the operating frequency and the operation mode of the particular procedure or desired effect on the tissue (i.e., contraction, coagulation or ablation). Typically, the peak-to-peak voltage will be in the range of 10 to 2000 volts, preferably in the range of 20 to 1200 volts and more preferably in the range of about 40 to 800 volts (again, depending on the electrode size, the operating frequency and the operation mode).

As discussed above, the voltage is usually delivered in a series of voltage pulses or alternating current of time varying voltage amplitude with a sufficiently high frequency (e.g., on the order of 5 kHz to 20 MHz) such that the voltage is effectively applied continuously (as compared with e.g., lasers claiming small depths of necrosis, which are generally pulsed about 10 to 20 Hz). In addition, the duty cycle (i.e., cumulative time in any one-second interval that energy is applied) is on the order of about 50% for the present invention, as compared with pulsed lasers which typically have a duty cycle of about 0.0001%.

It should be clearly understood that the invention is not limited to electrically isolated electrode terminals, or even to a plurality of electrode terminals. For example, the array of active electrode terminals may be connected to a single lead that extends through the probe shaft to a power source of high frequency current. Alternatively, the probe may incorporate a single electrode that extends directly through the probe shaft or is connected to a single lead that extends to the power source. The active electrode may have a ball shape (e.g., for tissue vaporization and desiccation), a twizzle shape (for vaporization and needle-like cutting), a spring shape (for rapid tissue debulking and desiccation), a twisted metal shape, an annular or solid tube shape or the like. Alternatively, the electrode may comprise a plurality of filaments, a rigid or flexible brush electrode (for debulking a tumor, such as a fibroid, bladder tumor or a prostate adenoma), a side-effect brush electrode on a lateral surface of the shaft, a coiled electrode or the like. In one embodiment, the probe comprises a single active electrode terminal that extends from an insulating member, e.g., ceramic, at the distal end of the probe. The insulating member is preferably a tubular structure that separates the active electrode terminal from a tubular or annular return electrode positioned proximal to the insulating member and the active electrode.

II. Power Supply

Figure 3:
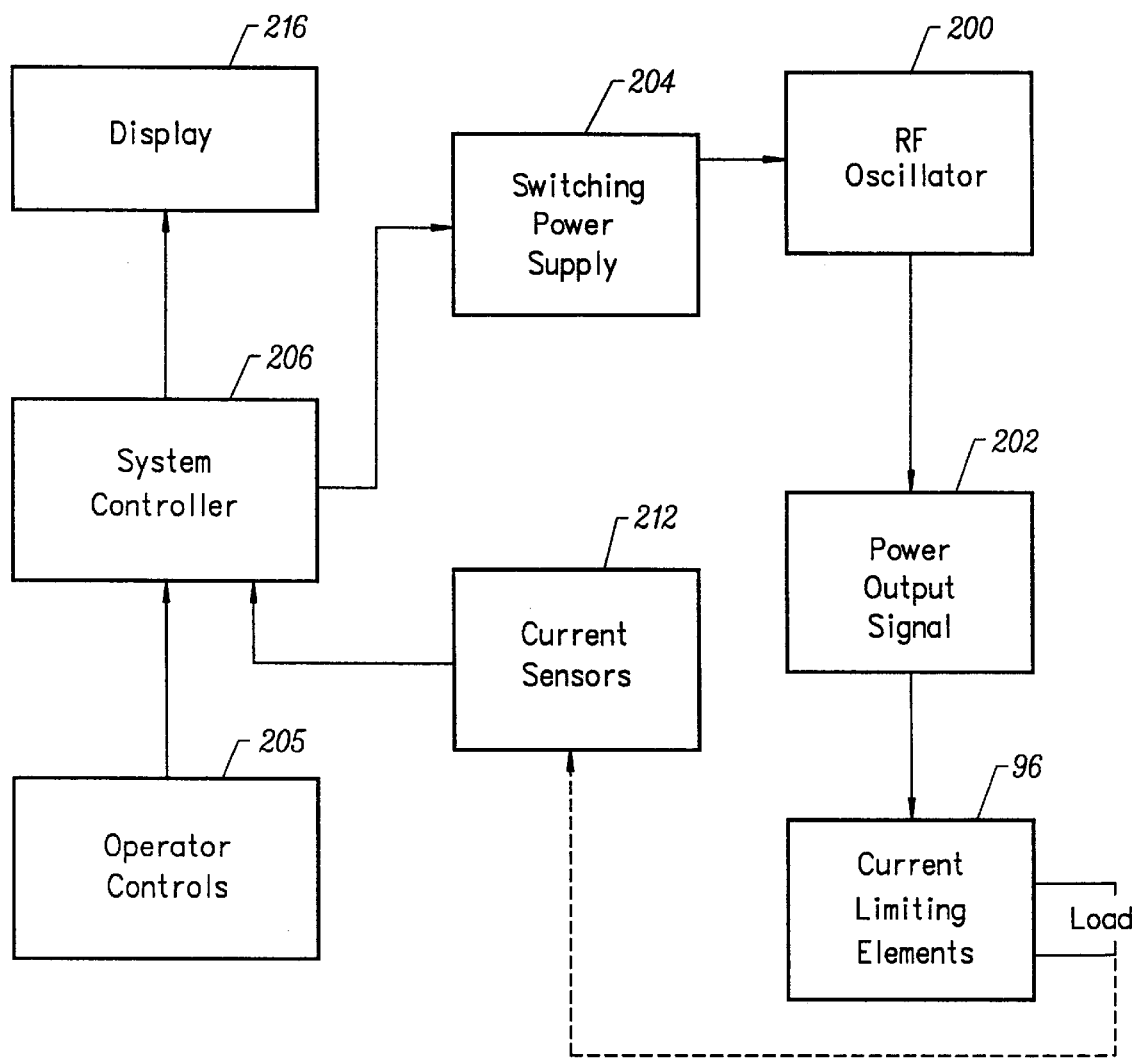
FIG. 3 is a block diagram functionally illustrating the main components of an exemplary generator according to the present invention.
Figure 4:
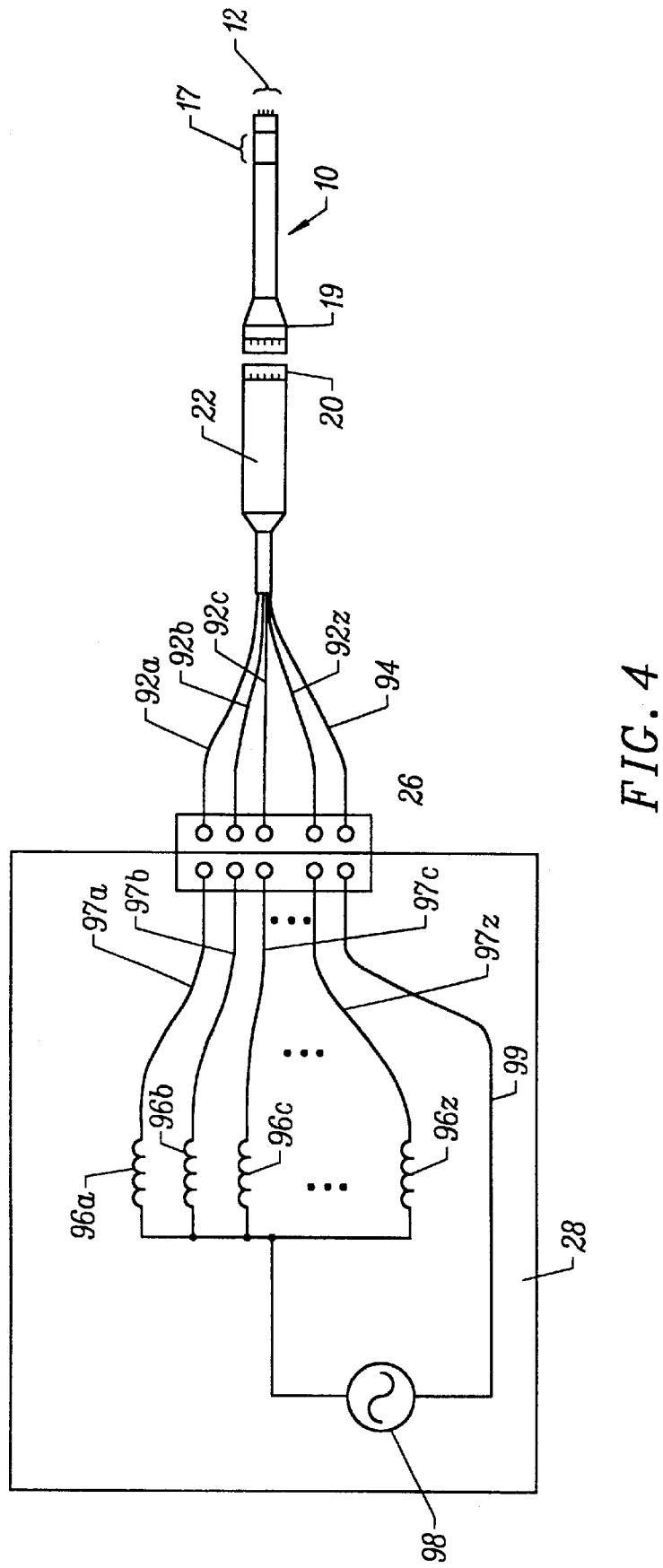
FIG. 4 is a schematic of an electrosurgical system, illustrating a plurality of inductors functioning as current limiting elements to a plurality of electrodes on the distal end of an electrosurgical probe.
Figure 5:
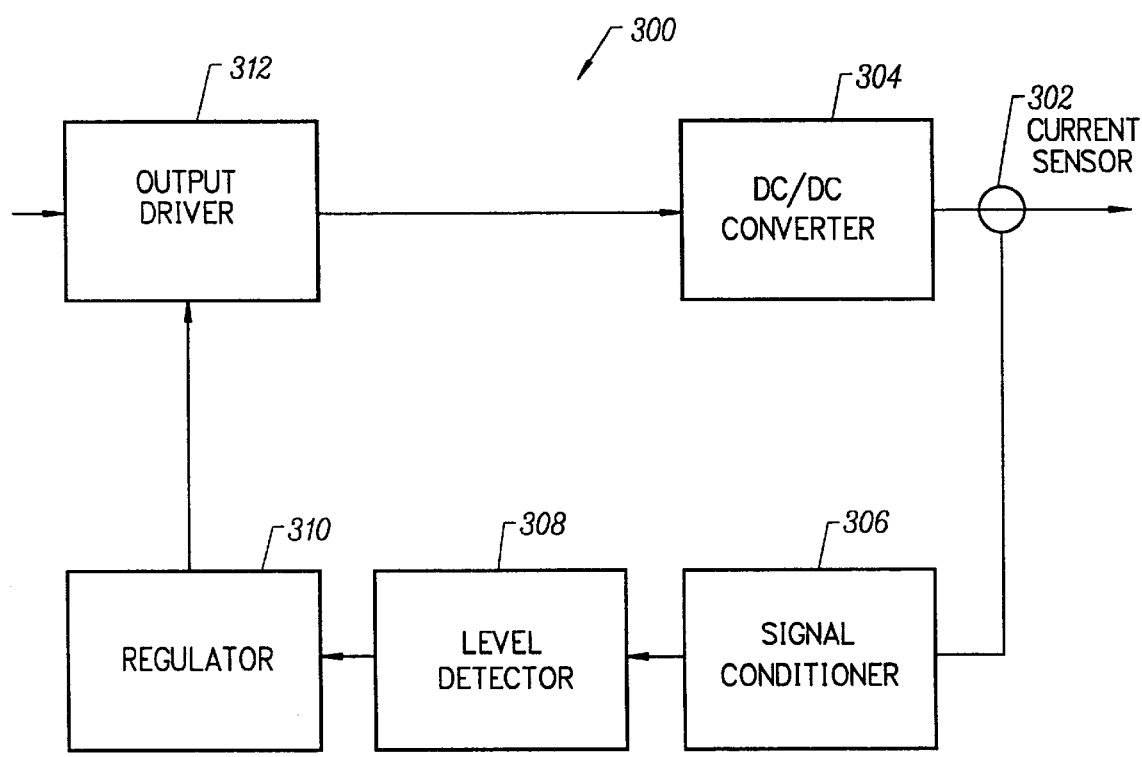
FIG. 5 is a block diagram of a power limiting device according to the present invention.

Referring now to FIGS. 3–5, a high frequency power supply constructed according to the principles of the present invention will now be described. The high frequency power supply of the present invention is configured to apply a high frequency voltage of about 10 to 500 volts RMS between one or more electrode terminals (and/or coagulation electrode) and one or more return electrodes. In the exemplary embodiment, the power supply applies about 70–350 volts RMS in the ablation mode and about 20 to 90 volts in a subablation mode, preferably 45 to 70 volts in coagulation mode (these values will, of course, vary depending on the probe configuration attached to the power supply and the desired mode of operation).

The preferred power source of the present invention delivers a high frequency current selectable to generate average power levels ranging from several milliwatts to tens of watts per electrode, depending on the volume of target tissue being heated, and/or the maximum allowed temperature selected for the probe tip. The power source allows the user to select the voltage level according to the specific requirements of a particular procedure, e.g., arthroscopic surgery, dermatological procedure, ophthalmic procedures, open surgery or other endoscopic surgery procedure.

As shown in FIG. 3, the power supply generally comprises a radio frequency (RF) power oscillator 200 having output connections for coupling via a power output signal 202 to the load impedance, which is represented by the electrode assembly when the electrosurgical probe is in use. In the preferred embodiment, the RF oscillator operates at about 100 kHz. The RF oscillator is not limited to this frequency and may operate at frequencies of at least 300 kHz, preferably 400 kHz, and more preferably 500 kHz. In particular, for cardiac applications, the RF oscillator will preferably operate in the range of about 300 kHz to about 600 kHz. The RF oscillator will generally supply a square wave signal with a crest factor of about 1 to 2. The power output signal 202 is designed to incur minimal voltage decrease (i.e., sag) under load. This improves the applied voltage to the electrode terminals and the return electrode, which improves the rate of volumetric removal (ablation) of tissue.

Power is supplied to the oscillator 200 by a switching power supply 204 coupled between the power line and the RF oscillator rather than a conventional transformer. The switching power supply 240 allows the generator to achieve high peak power output without the large size and weight of a bulky transformer. The architecture of the switching power supply also has been designed to reduce electromagnetic noise such that U.S. and foreign EMI requirements are met. This architecture comprises a zero voltage switching or crossing, which causes the transistors to turn ON and OFF when the voltage is zero (one embodiment of this architecture is shown in detail in FIGS. 18 and 19). Therefore, the electromagnetic noise produced by the transistors switching is vastly reduced. In an exemplary embodiment, the switching power supply 204 operates at about 100 kHz.

A controller 206 coupled to the operator controls 208 (i.e., foot pedals and voltage selector) and display 210, is connected to a control input of the switching power supply 204 for adjusting the generator output power by supply voltage variation. The controller 206 which may be a microprocessor or an integrated circuit. The power supply may also includes one or more current sensors 212 for detecting the output current. The power supply is preferably housed within a metal casing which provides a durable enclosure for the electrical components therein. In addition, the metal casing reduces the electromagnetic noise generated within the power supply because the grounded metal casing functions as a "Faraday shield", thereby shielding the environment from internal sources of electromagnetic noise.

The power supply generally comprises a main or mother board containing generic electrical components required for many different surgical procedures (e.g., arthroscopy, urology, general surgery, dermatology, neurosurgery, etc.), and a daughter board containing application specific current-limiting circuitry (e.g., inductors). The daughter board is coupled to the mother board by a detachable multi-pin connector to allow convenient conversion of the power supply to, e.g., applications requiring a different current limiting circuit design. For arthroscopy, for example, the daughter board preferably comprises a plurality of inductors of about 200 to 400 microhenries, usually about 300 microhenries, for each of the channels supplying current to the electrode terminals (see FIG. 4).

Alternatively, in one embodiment, current limiting inductors are placed in series with each independent electrode terminal, where the inductance of the inductor is in the range of 10 uH to 50,000 uH, depending on the electrical properties of the target tissue, the desired tissue heating rate and the operating frequency. Alternatively, capacitor-inductor (LC) circuit structures may be employed, as described previously in co-pending PCT application No. PCT/US94/05168, the complete disclosure of which is incorporated herein by reference. Additionally, current limiting resistors may be selected. Preferably, these resistors will have a large positive temperature coefficient of resistance so that, as the current level begins to rise for any individual electrode terminal in contact with a low resistance medium (e.g., saline irrigant or conductive gel), the resistance of the current limiting resistor increases significantly, thereby minimizing the power delivery from said electrode terminal into the low resistance medium (e.g., saline irrigant or conductive gel).

Power output signal may also be coupled to a plurality of current limiting elements 96, which are preferably located on the daughter board since the current limiting elements may vary depending on the application. FIG. 4 illustrates an arrangement that may be used in arthroscopic procedures with a multi-electrode probe. As shown, a high frequency power supply 28 comprises a voltage source 98 which is connected to a multiplicity of current limiting elements 96a, 96b, . . . 96z, typically being inductors having an inductance in the range of about 100 to 5000 microhenries, with the particular value depending on the electrode terminal dimensions, the desired ablation rates, and the like. Capacitors having capacitance values in the range of about 200 to 10,000 picofarads may also be used as the current limiting elements. It would also be possible to use resistors as current limiting elements. The current limiting elements any also be part of a resonant circuit structure, as described in detail in PCT/US94/05168.

A. Power Limiting

The power supply 28 of the present invention may include power limiting devices to protect attached electrosurgical probes from excessive power delivery and to sustain controlled probe operation. Power is the time rate of transferring or transforming energy, and for electricity, power is measured in watts, where one watt is the power to create energy at the rate of one joule per second. Referring to FIG. 5, the power limiting device 300 is designed to reduce the power drawdown from the power supply 28 when an attached device such as a monopolar or bipolar surgical instrument is not engaging body tissue or draws excessive power. For example, excessive power is delivered from the power supply 28 if the RF surgical instrument or probe is in saline and is not engaging target tissue. Device 300 conveniently conserves power used in the probe without completely deactivating the power supply 28 or requiring the user to manually reduce power. Excessive power draw will overheat the power supply and corrupt power supply performance. Device 300 also acts as a safety feature by reducing the stray emission of energy when the probe is in transit through the body to a target site.

Figure 6:
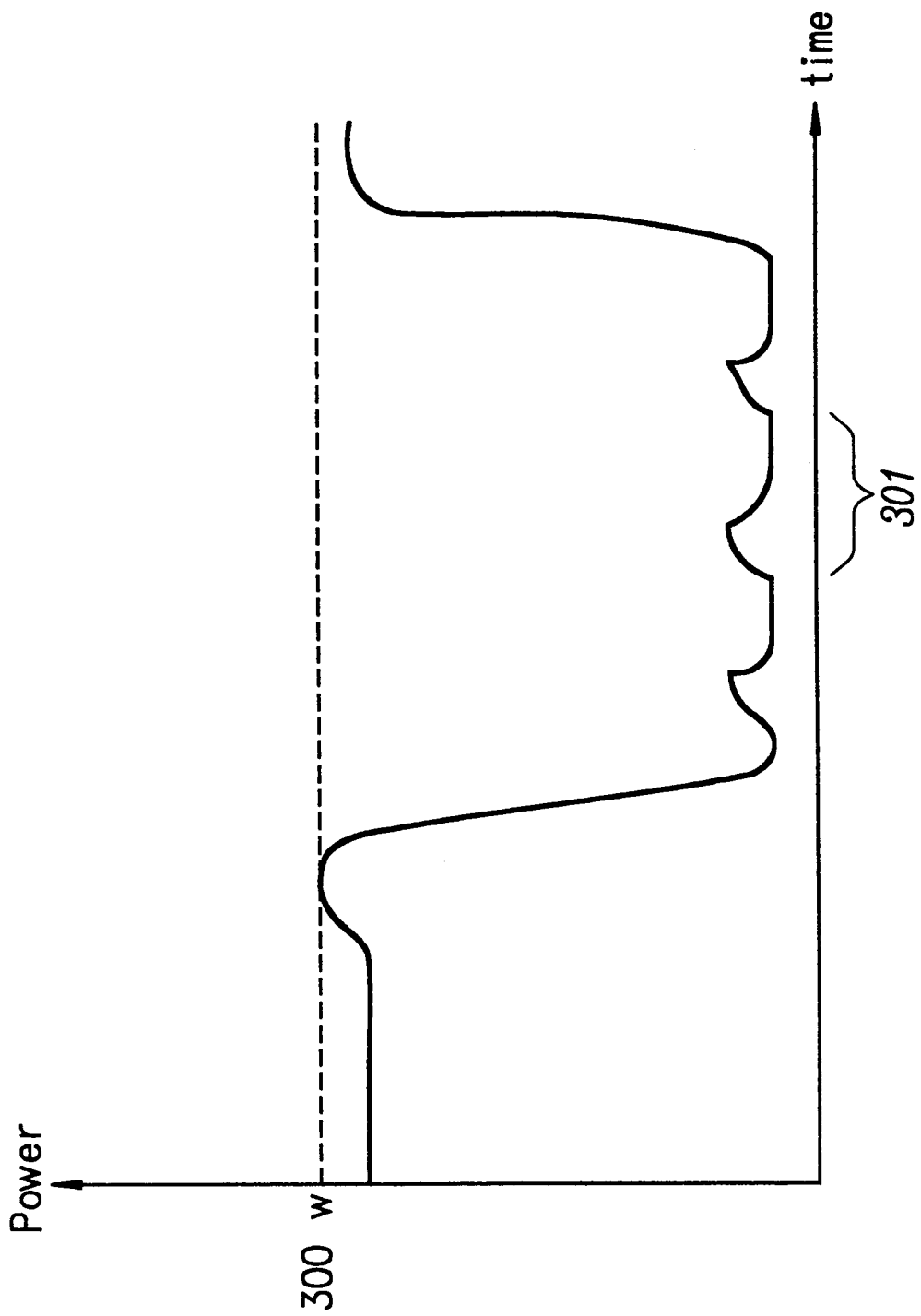
FIG. 6 is a graph of the power output of the power supply during normal operations and standby mode.

In general terms, the power limiting device 300 operates on a continuous basis to detect excessive power output. The device 300 is responsive to the "total power" delivered by the device. FIG. 6 shows the power output of the power supply 28 when an excessive power is detected. Device 300 limits the overall output power from the controller to be lower than about 240–360 watts, preferably about 300 watts. Once power output exceeds a predetermined threshold level, the device 300 then operates on a duty cycle or periodic detection cycle 301 between about 50 and 300 ms, where the device 300 checks every cycle to determine if it is safe to resume power output. Preferably, the device 300 has a fixed duty cycle wave form and includes a fixed periodical pulsing circuit which is about 10 ms on and 90 ms off. Once the fault condition is gone, power output returns to operating levels.

Figure 8A:
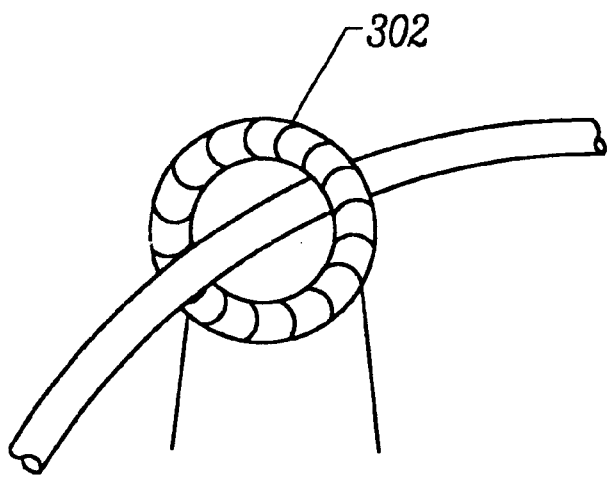
FIGS. 8A–8C show various embodiments of a current sensor.
Figure 8B:
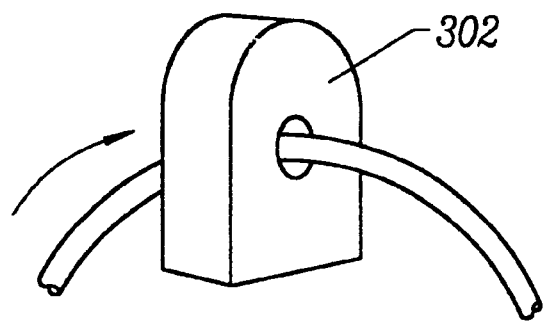
Figure 8C:
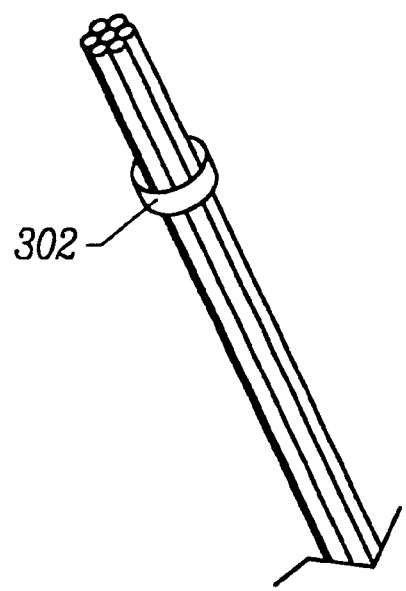

In one embodiment (FIG. 5), the device 300 uses a current sensor 302 attached to the output electrodes to derive the power output of the power supply 28. The current limit, which may be set at any desire level, is about 5 amps for a 300 watt power limit when voltage is set at about 60V. When current output reaches 5 amps, the device 300 reduces the output of the power supply to a standby mode. Once in standby mode, the power supply preferably has a pulsatile power output. As shown in FIG. 8, the device 300 allows the current output to be activated during each duty cycle to determine if the power supply may return to normal operation.

Figure 7:
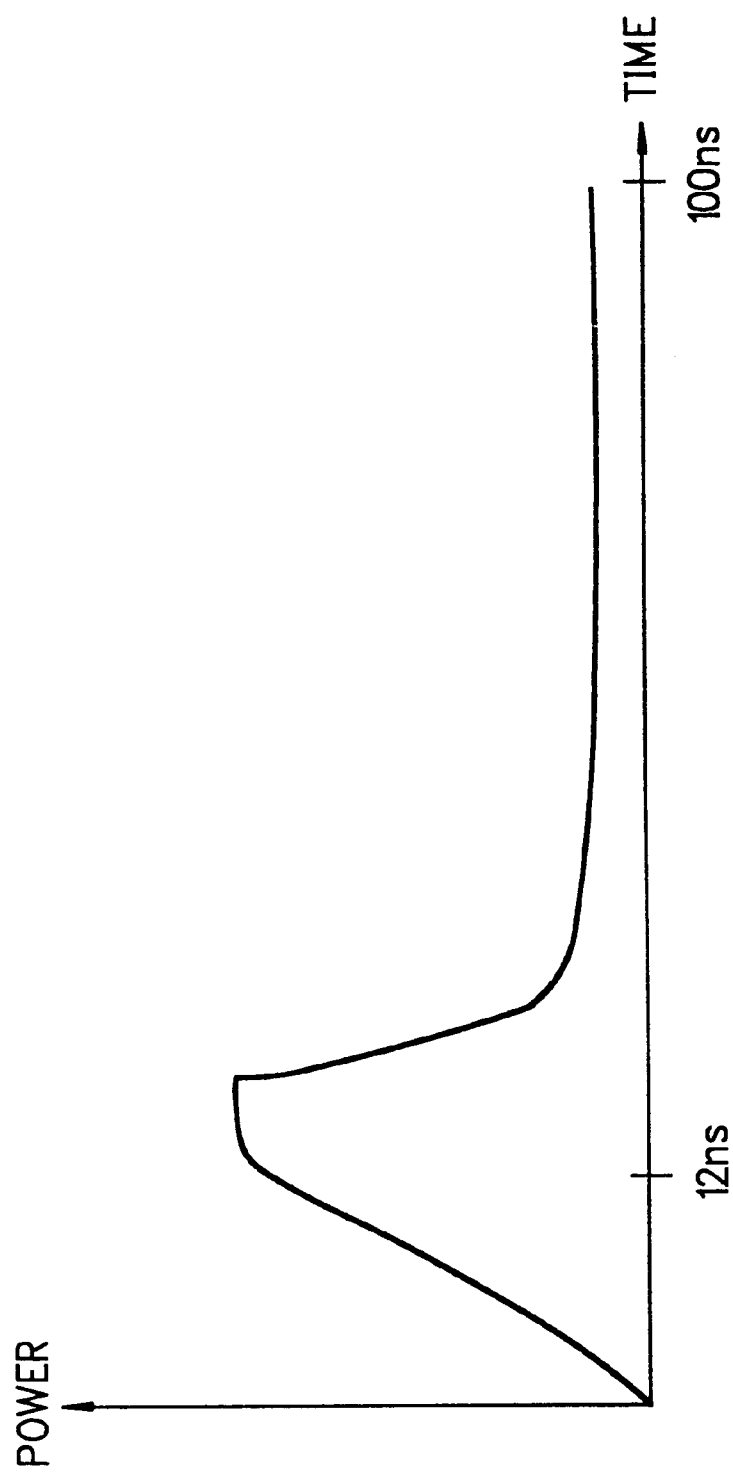
FIG. 7 is a graph of the power output of the power supply in a low power, pulsatile mode.

When in the standby mode, the pulsatile power output may be described as shown in FIG. 7. In the pulsatile mode, the duty cycle is about 10–15 ms on, preferably about 12 ms on, and about 85–90 ms off, preferably about 88 ms off. This creates a cycle of about 100 ms, during which time, power is increased and then reduced if the probe senses that it is not in the vicinity of body tissue or other higher impedance material. This sensing step is the initial portion of the duty cycle where current is activated for a period of time, described as being between 10–15 ms. If current again reaches the 5 amp level or some other predetermined level, the output is reduced and the device 300 waits for the next duty cycle. The total power output during this short period is only about 10 watts. However, the current output is sufficient to show that the fault condition still exists. Thus, when in the standby mode, the device 300 tests for potentially excessive power output with a fault condition that occurs without actually reaching the power level against which the device is protecting. This pulsatile power output continues until power drawdown returns to within acceptable ranges (FIG. 6). The power limiting reduces power output on a fault condition that is current based (so long as there is constant voltage).

Alternatively, the power limiting device 300 in the standby mode checks the impedance (instead of current) encountered by the probe every 100 ms or over some other interval selected by the user. As long as the probe is in a low impedance environment and impedance is below a predetermined level, the power supply will operate in the pulsatile mode, never fully activating to therapeutic power levels such as for ablation or coagulation. The low impedance is indicative of a potential over power scenario. In alternative embodiments, the device 300 may check the impedance over variable time intervals that change as desired. When the probe reaches a target site or comes in the vicinity of higher impedance tissue, in one embodiment, a higher impedance is noted by a drop in current draw (i.e. power draw) from the probe, signaling the regulator or logic unit 310 to increase power on the current or the next duty cycle. This brings the power supply out of the pulsatile mode. The power limiting device 300, however, will continue to check the impedance encountered every duty cycle.

Referring to FIGS. 5, a preferred embodiment of the device 300 comprises of at least one current sensor 302 detecting the current output from DC/DC converter 304. The current sensor 302 may be configured as one sensor for one electrode or one sensor for a plurality of electrodes. In the present embodiment, one sensor 302 is used for six electrodes on the probe, although more preferably one sensor is used for three electrodes. Typically, the sensors 302 (noted as T1, T4, T5, etc.) are configured to wrap around the electrodes as shown in FIG. 8. Signals from sensors 302 are passed through a plurality of rectifying diodes and capacitors which filter and condition the typically analog signal from the current sensor. In the block diagram of FIG. 5, these diodes and components are represented by signal conditioner 306. The conditioned signal from the sensor 302 is then passed to a voltage comparator 308. The comparator 308 determines if the current output has exceed the predetermined threshold level. A logic unit 310 then determines power of output drive 312 based on the value of the output current compared to a predetermined current value. In the standby or power limited mode, the logic unit 310 of the device 300 will preferably duty cycle the output from output drive 312. Although the logic unit 310 is preferably an integrated circuit such as a Field Programmable Gate Array (FPGA) to maximize cost efficiency, it should be understood that other devices such as computers or microprocessors may also be used to perform the required logic functions.

Figure 9A:
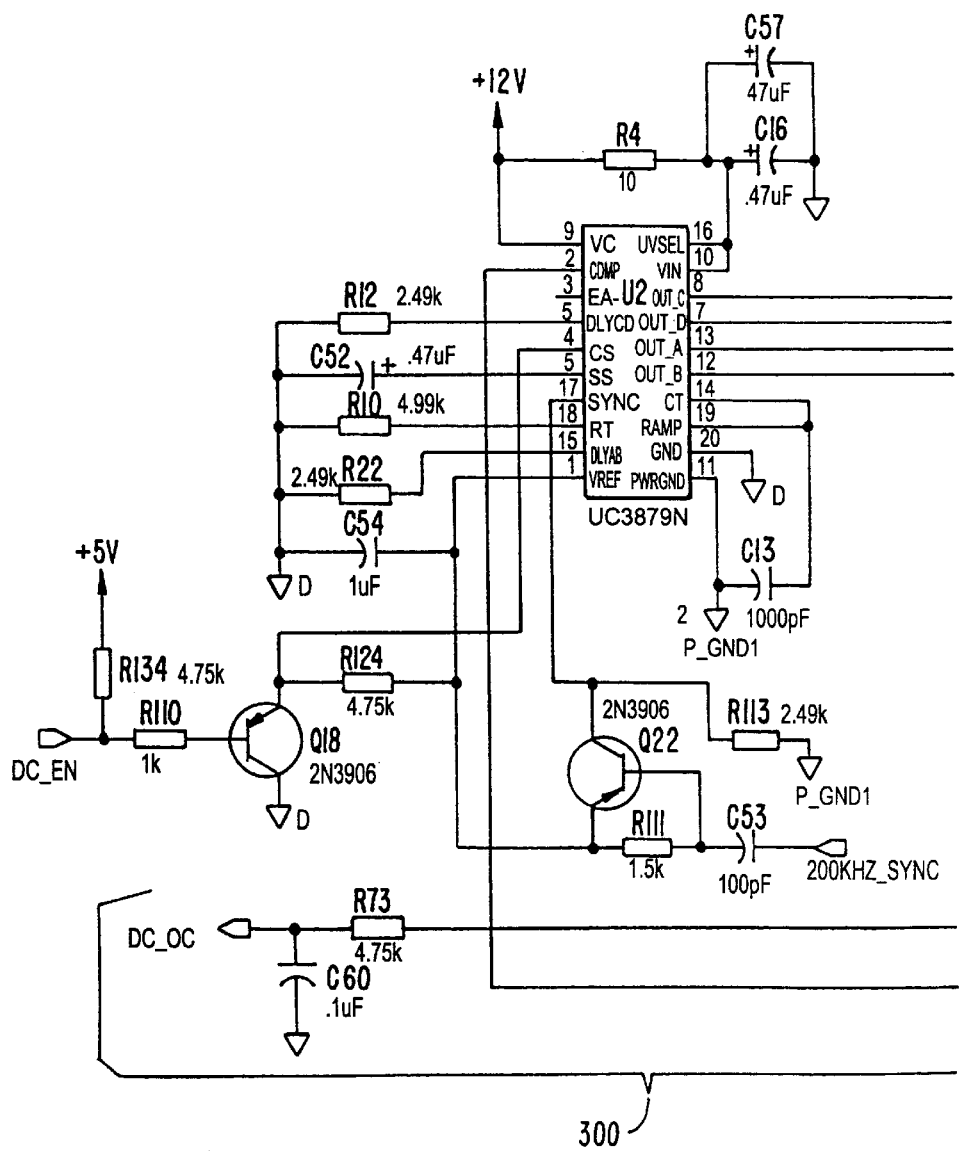
FIG. 9 is a circuit schematic of an exemplary embodiment of a power limiting device.
Figure 9B:
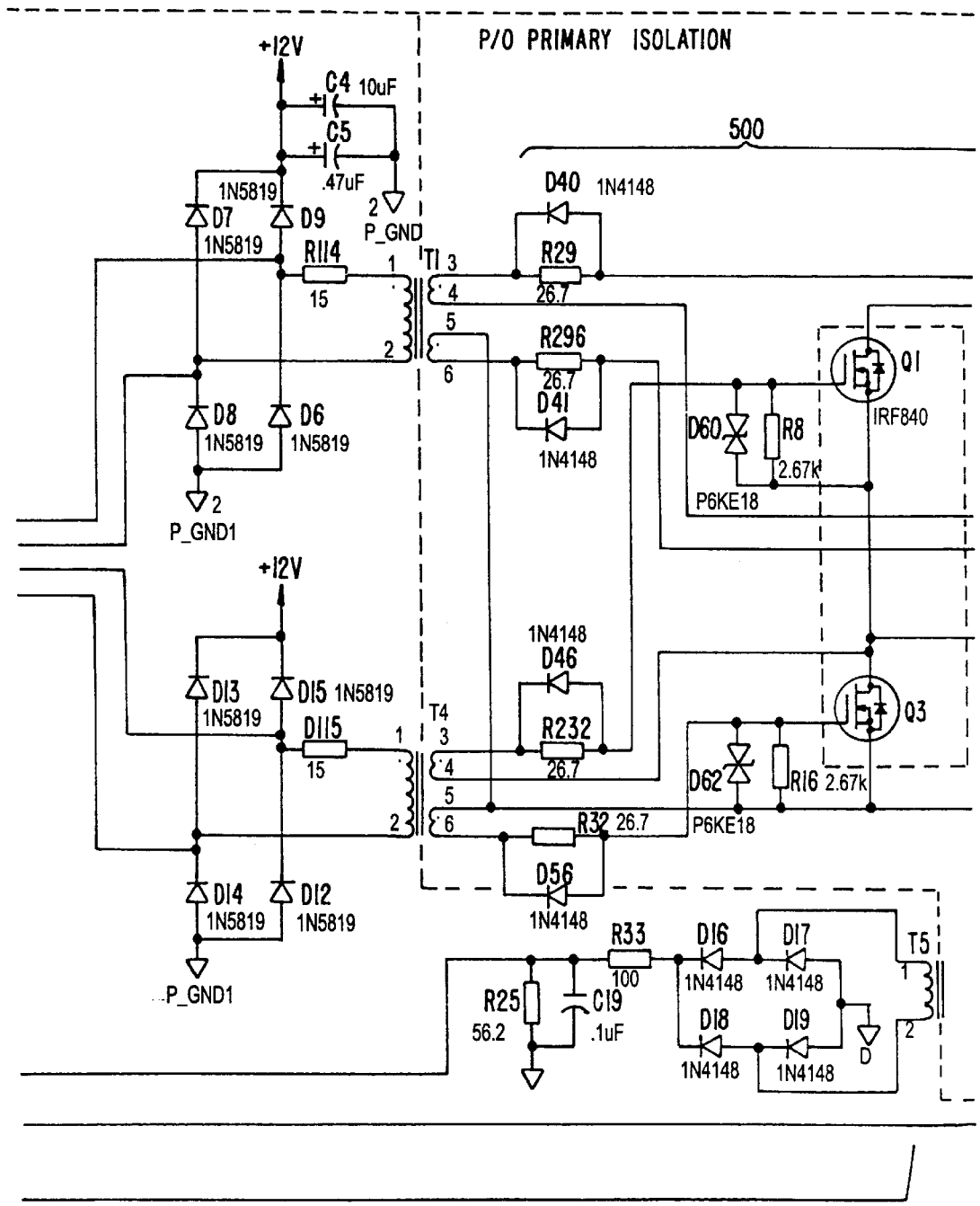
Figure 9C:
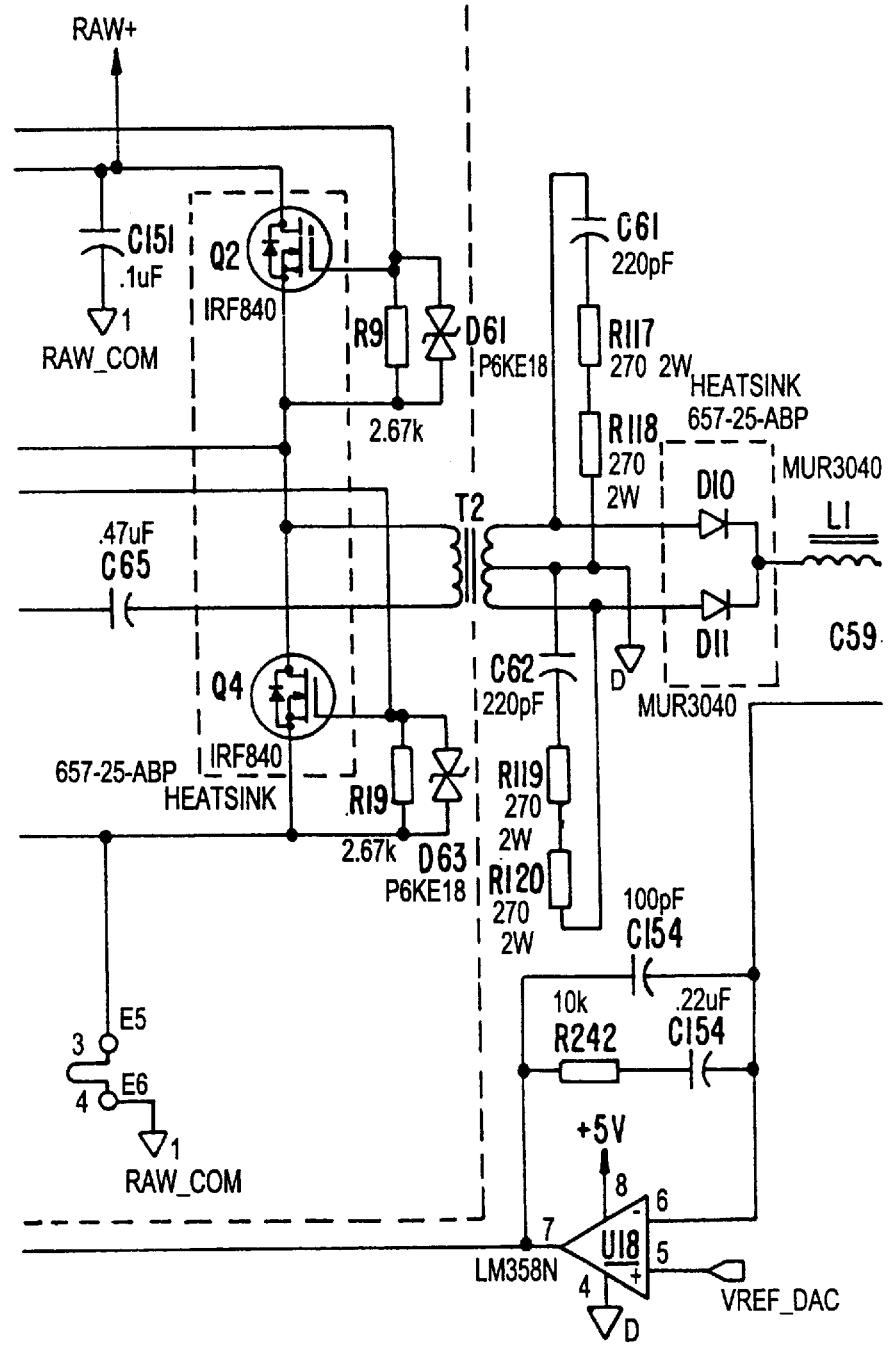

FIG. 9 shows an exemplary embodiment of power limiting device 300. The circuit diagram shows that overcurrent is sensed by T5. It is rectified and filtered by D16, D17, D18, D19, R33, and C19 etc. The rectified and filtered signals are fed into voltage comparator which determines if power threshold has been reached. The output of the comparator is fed into the FPGA which controls the power supply 28 to the power limiting mode (e.g. it turns of DC/DC converter 10 ms on and 90 ms off). Device 300 includes an converter of a full-wave bridge arrangement with all four switching element driven by a single transformer. It is capable, through the antiparallel diodes within the MOSFETs, of four-quadrant operation, returning reactive load energy to the power supply for self-protection. 100 kHz sync arrives as 500 nanosecond pull-up pulses from a differentiation network connected to the FPGA. The FPGA also exerts direct on/off control via DC_EN. The output smoothly ramps to regulation when allowed by the FPGA. Options for current limiting are provided. Both linear and digital (pulsatile) limiting are possible. Current limits may also respond to FPGA commands and change under logic control. The inverter is running at zero voltage switching mode to reduce EMI and indirectly reduces leakage current. A cycle-by-cycle current limit circuit serves to protect the switching elements from energy stored in filter and bypass capacitors. Cycle-by-cycle current limit control is applied by the FPGA removing the gate drive. The inverter runs at a fixed 50% duty cycle whenever drive (of about 100 kHz or other) from the FPGA is available. The inverter is running at zero voltage switching mode to reduce EMI and indirectly reduces leakage current.

B. Spark Limiting

The power supply 28 of the present invention may also include a spark limiting device 330 to prevent sudden current spikes which may char or otherwise damage the RF probe and surgical target site. For example, when an RF probe attached to the power supply touches a metallic object, the impedance encountered by the probe (relative to human tissue) decreases suddenly and this undesirably draws a large amount of current from the power supply. This sudden current increase may create sparks between the probe and the metal object. The large amount of current passing through the probe will likely char items along the electrical pathway and may melt electrodes on the electrosurgical probe.

Figure 10:
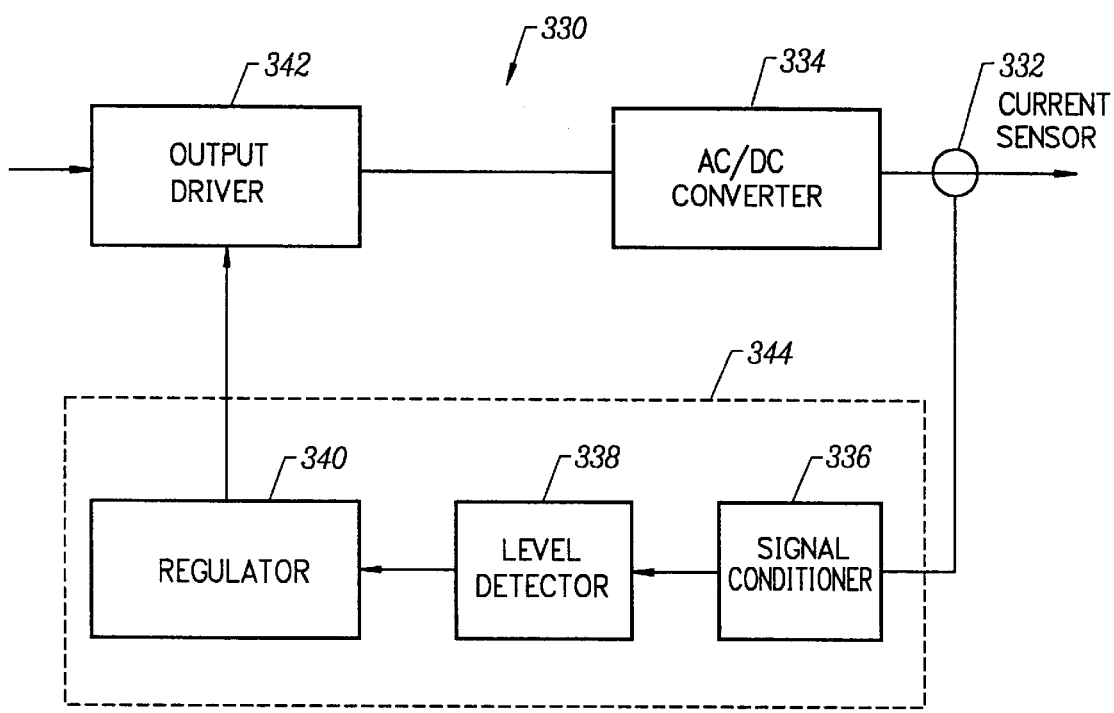
FIG. 10 is a block diagram of a spark limiting device according to the present invention.

Referring now to FIG. 10, the spark limiting device 330 will be described in detail. In general terms, the spark limiting device 330 will reduce current output to zero when an extremely low impedance source such as a metal screw or a metal cannula creates a high current drawdown. The spark limiting device 330 is located much closer to the output electrode. This reduces the delay of the device 330 and allows the device to respond more quickly. The spark limiting device 330 is directed to reduce current output to prevent sparking, not total power output. Although the block diagram of FIG. 10 appears similar to that of the power limiting device 300, the spark limiting device 330 is not a fixed periodical pulsing circuit of the type described in FIG. 9. The spark limiting device 330 preferably processes continuous signals, such as analog signals, from the current sensor 332. The spark limiting device 330 continuously monitors current fluctuations of the power output of converter 334 (typically an AC/DC converter). The continuous flow of signal in the spark limiting device 330 allows it to detect the sudden increase in current almost instantaneously and almost certainly before the isolated, power limiting device 300. Current output is preferably turned off after an overcurrent is detected.

Figure 11:
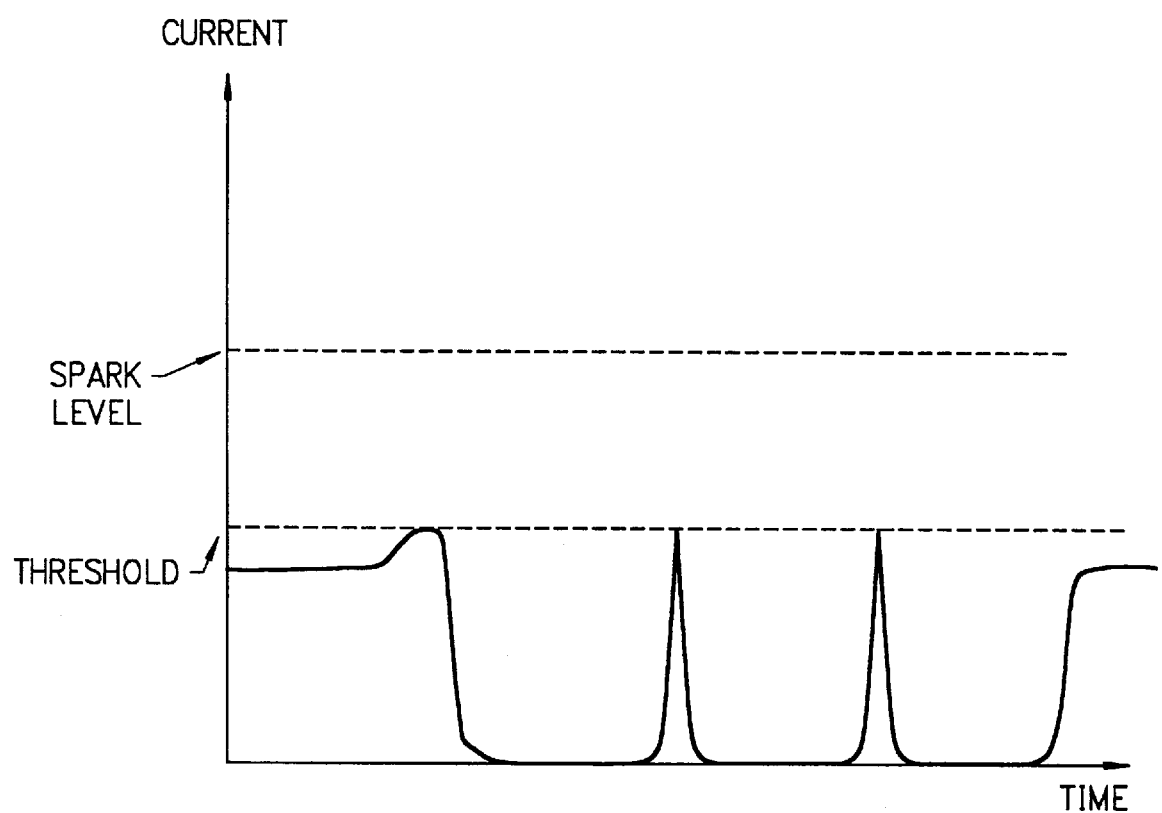
FIG. 11 is a chart of the current output of a spark limiting device according to the present invention.

The current output during normal therapeutic operation may be in the range of 0.2 amperes or less. The spark limiting device 330 preferably interrupts output when current exceeds about 1.0 to 3.0 amperes. These current levels are insufficient to cause sparking, but enough to warrant concern over potential sparking. When current exceeds levels higher than those stated, the device 330 will preferably prevent any current output from the probe. The output of the power supply 28 is similar to that of FIG. 11. In one embodiment, the spark limiting device 330 has a built-in delay device that turns off current output for a duration of 2–90 ms. Preferably, the delay is programmed into the FPGA. At the end of the delay period, the device 330 will allow current to flow through the probe, albeit at extremely low power, to detect if the extremely low impedance state still exists. If current again exceeds the threshold level of about 1.0 to 3.0 amperes (FIG. 11), the device 330 will zero the output of the power supply and pause for the built-in delay. This delay acts in some ways to give the spark limiting device a duty cycle-like operation.

It should be understood that although no current, preferably, is being emitted from the probe during the delay period, the power supply does not shutoff. This is particularly useful as this eliminates down time associated with restarting the power supply from poweroff. As soon as the probe is removed from the area of extremely low impedance, the spark limiting device 330 will allow power to flow from the RF probe as usual. Preferably, as long as the probe is exposed to the low impedance source, the device 330 will not allow power to be transmitted. Of course, it may be possible to configure the spark limiting device 330 to allow a low level of current to be emitted, versus shutting off the power output completely.

Figure 12:
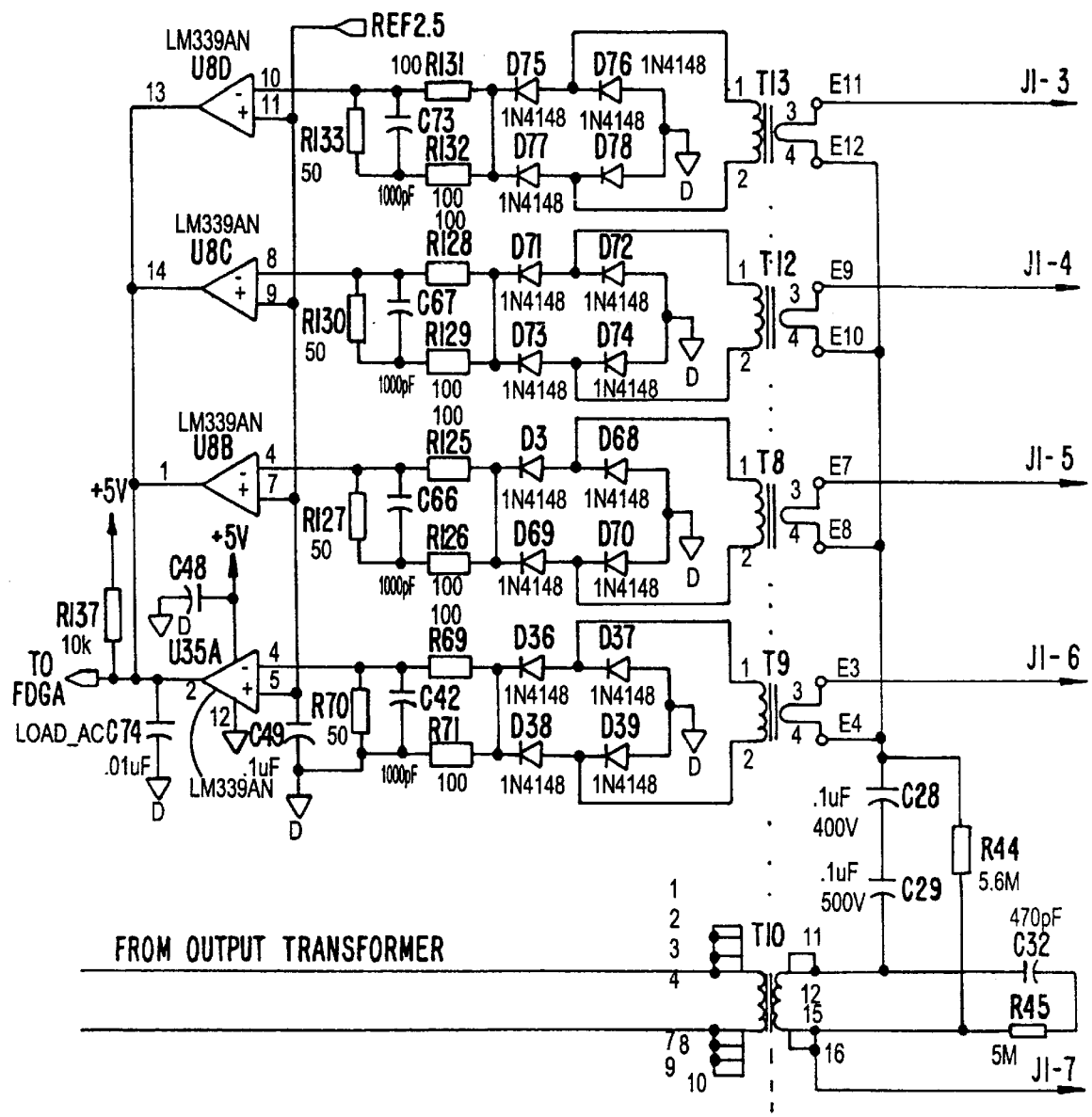
FIG. 12 is a circuit schematic of an exemplary embodiment of a spark limiting device.

The block diagram of FIG. 10 shows that the spark limiting device 330 includes a signal conditioner 336, a level detector 338, a regulator or logic unit 340, and an output driver 342 (such as an RF source known in the art). Although the preferred embodiment of the spark limiting device 330 is based on analog signals, it should be understood that the device 330 may be adapted to used analog signals or digital signals with extremely short duty cycles to approximate a continuous system. The logic device 340, level detector 338, and signal conditioner 336 may all be combined into a single device or processor as indicated by the dotted line 344. The same may also apply to the power limiting device 300 which has components that may be integrated together. Referring to FIG. 12, a circuit diagram of the spark limiting device 330 is shown. The current sensors 332 are denoted by elements T8, T9, T12, and T13. The diodes D36–D76 and resistors/capacitors R131–R133/C73 etc. are used to condition the analog signal to remove noise and other undesirable qualities. A voltage comparator U8D and the FPGA, corresponding to level detector 338 and logic device 340, are used to determine if the output current detected by sensor 332 is above a predetermined level.

Figure 13:
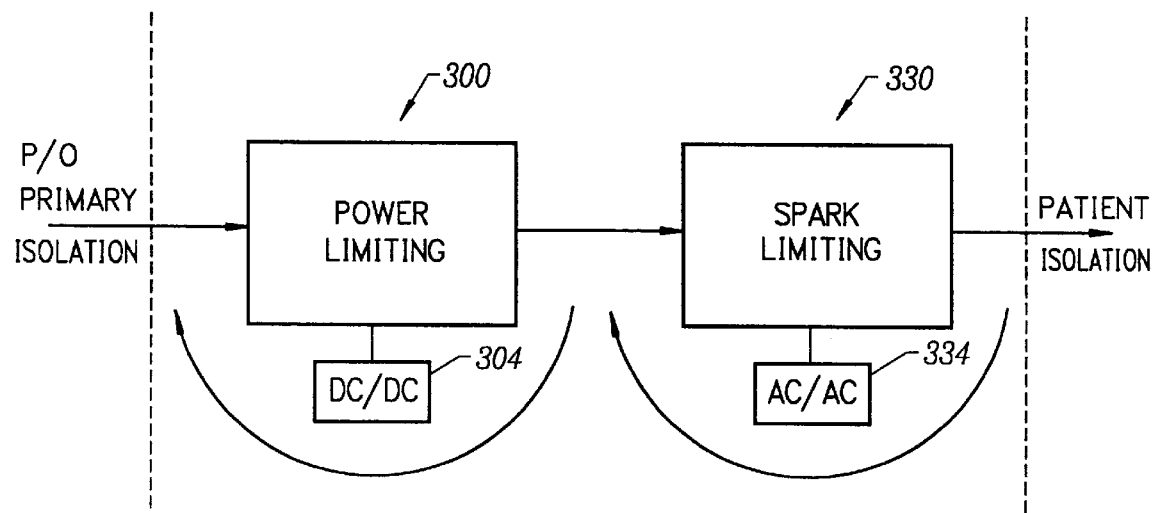
FIG. 13 is a block diagram of the relationship between power limiting and spark limiting devices.
Figure 14A:
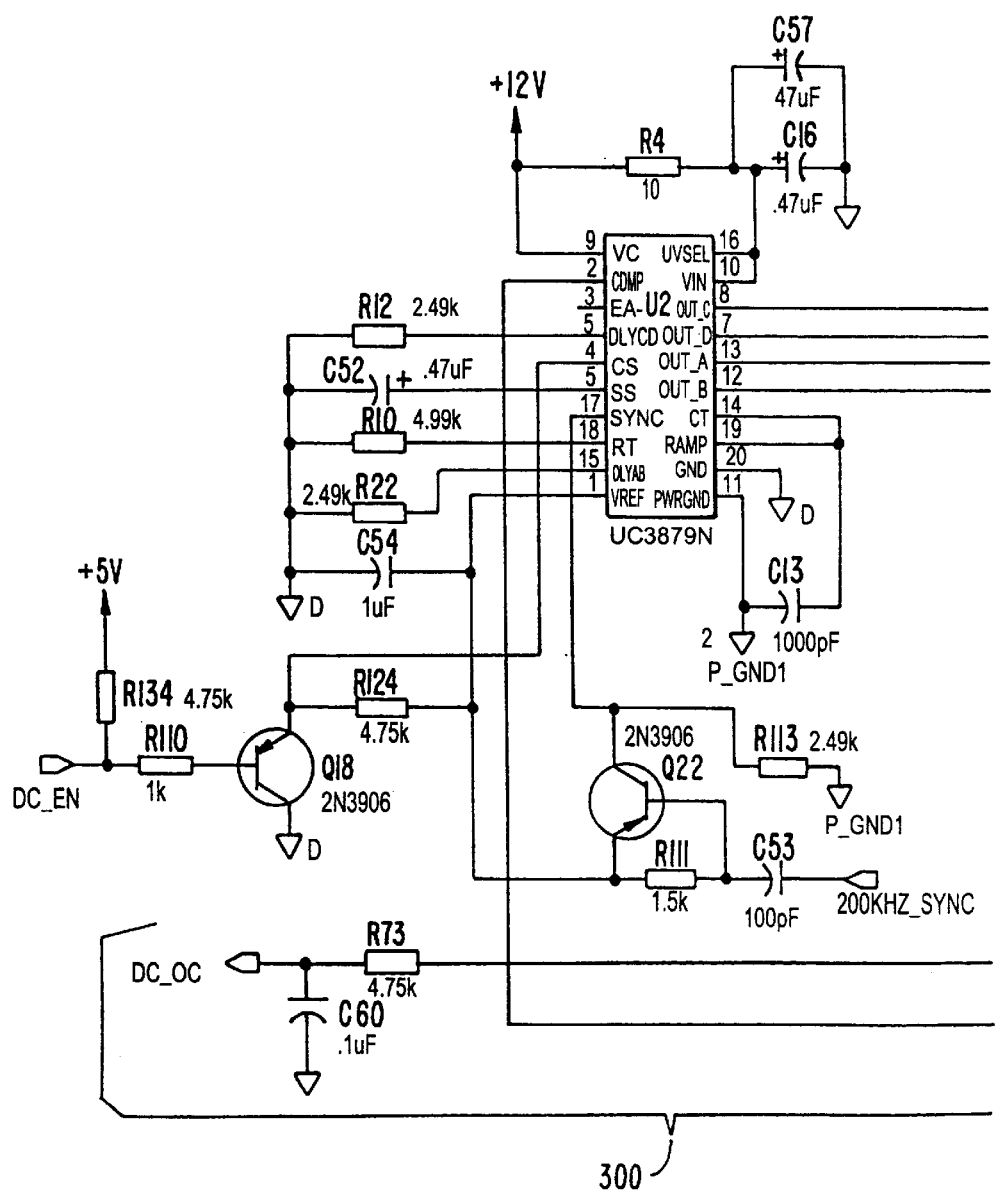
FIG. 14 is a circuit schematic showing both the power limiting and spark limiting devices.
Figure 14B:
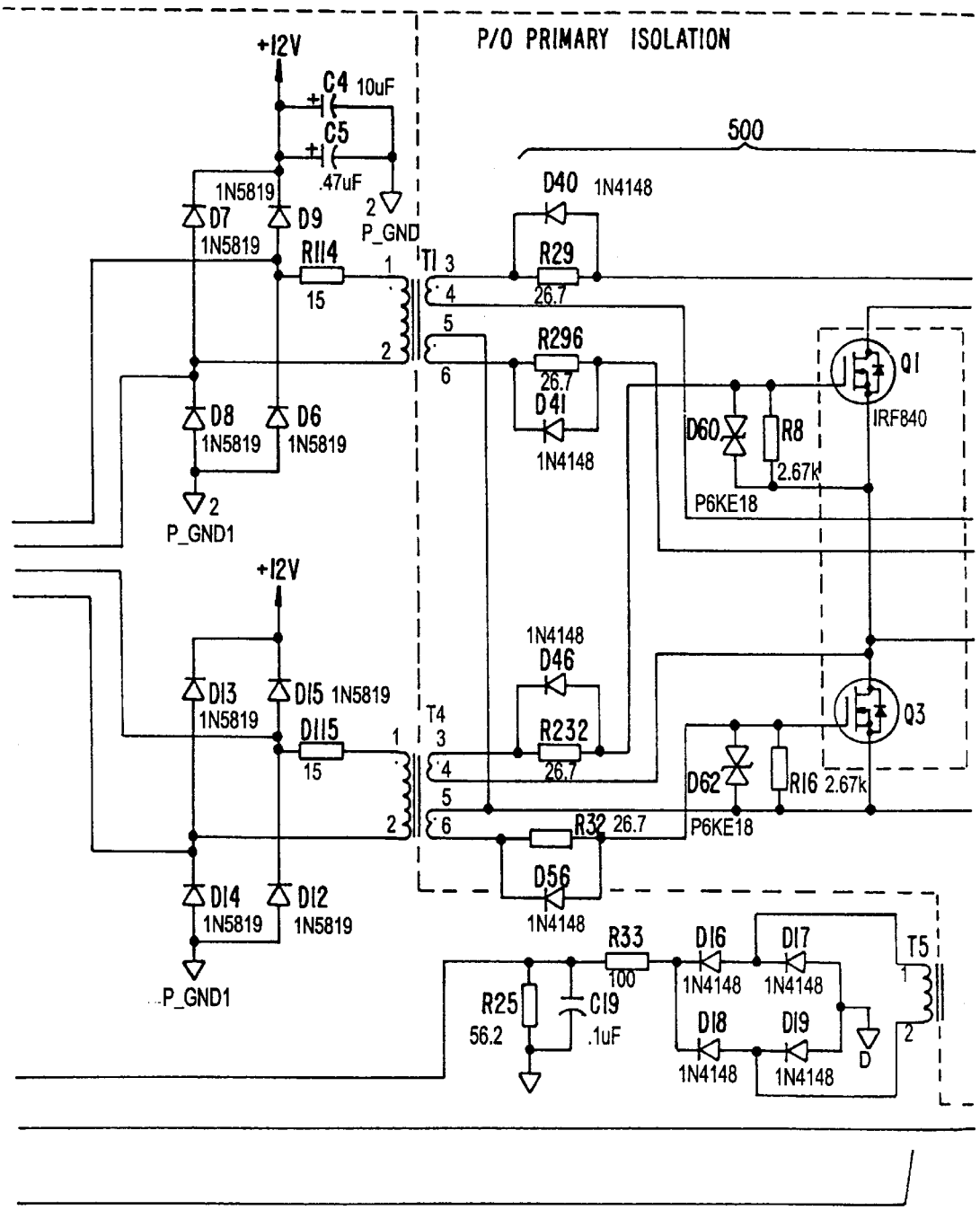
Figure 14C:
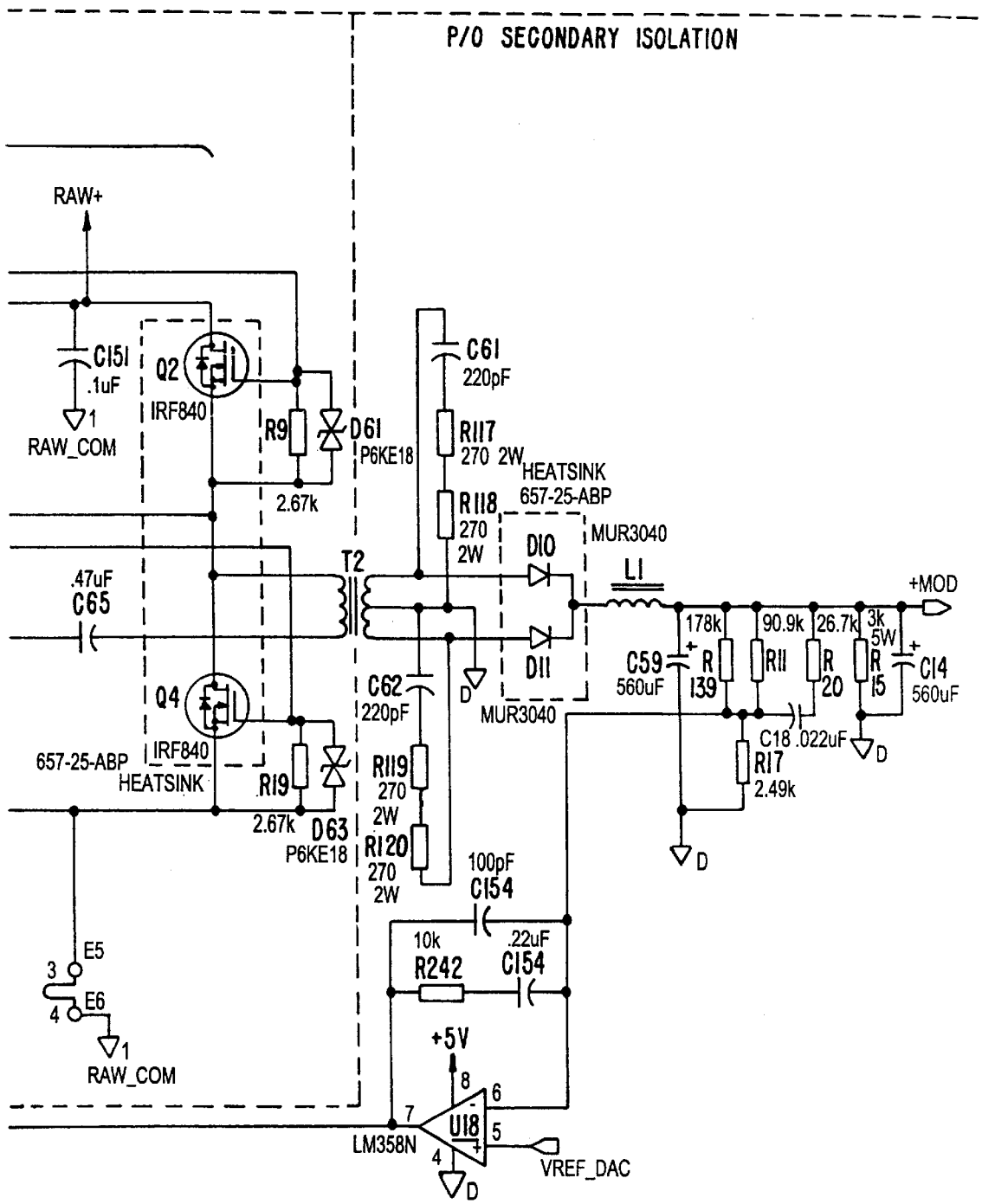
Figure 14D:
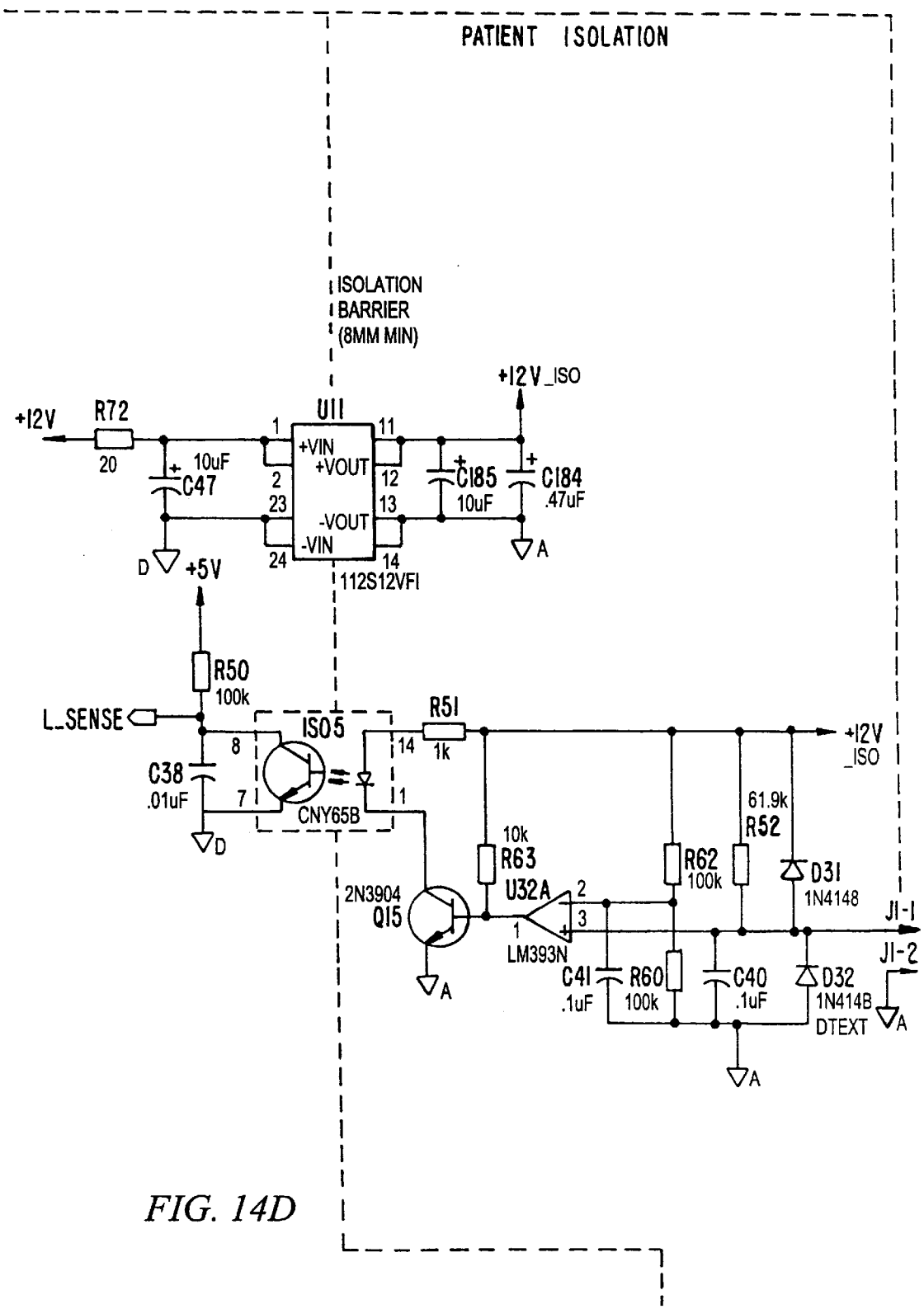
Figure 14E:
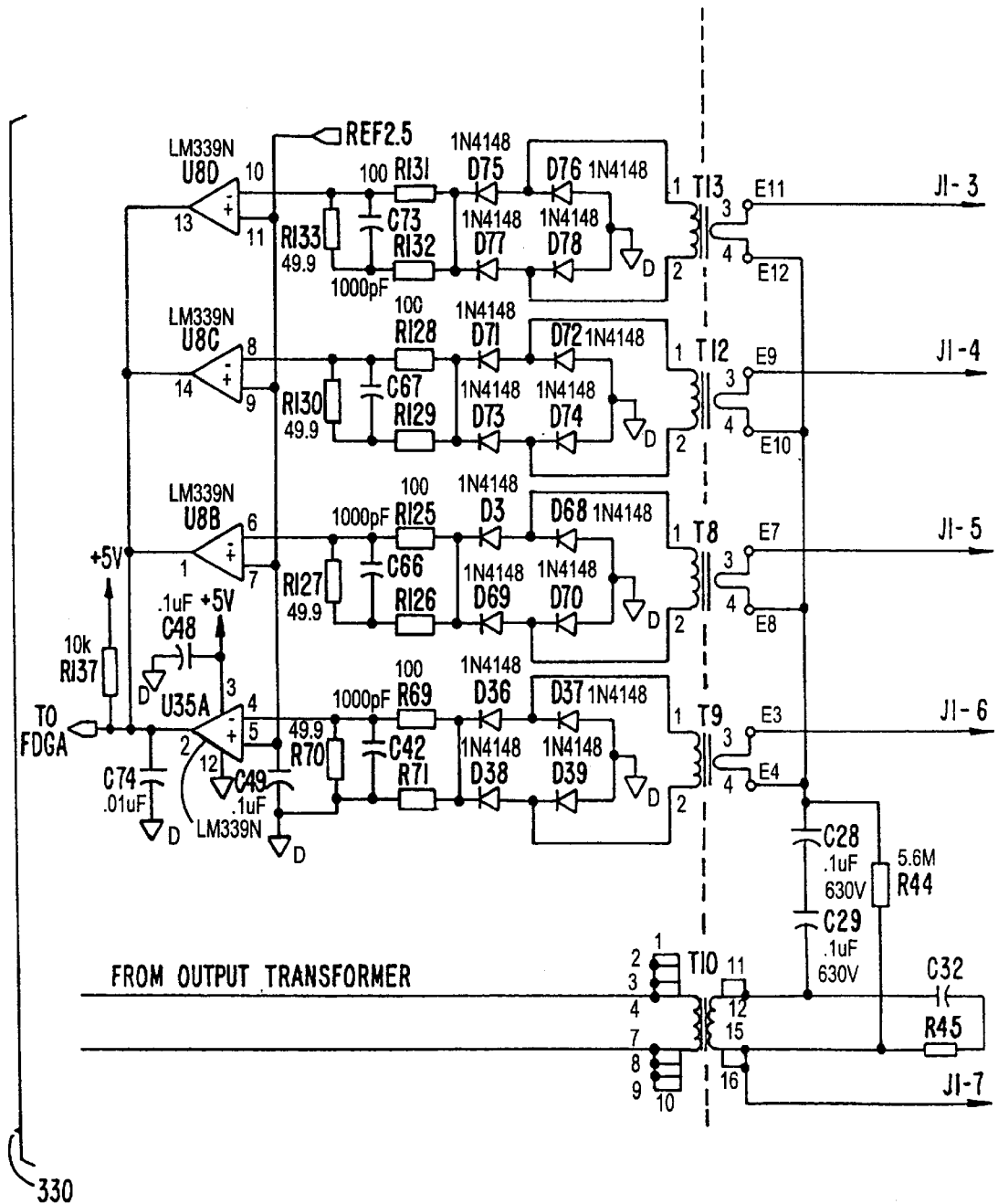

Although the power limiting device 300 and the spark limiting device 330 may be used individually, it is understood that the two devices may also be used concurrently in the power supply. In a preferred embodiment, the power supply of the present invention has the power limiting device 300 and the spark limiting device 330 arranged in a serial configuration as shown in FIGS. 13–14. This configuration provides for the circuit isolation mandated by safety regulations for medical device power supplies. As shown in FIG. 14, the power supply 28 has P/O primary isolation, P/O secondary isolation, and patient isolation. Using devices 300 and 330 also provides protection.for both converters (DC/DC and DC/AC) used to provide stability of the power output. Due to the various isolation barriers required to meet safety and regulatory standards for medical device power supplies, the spark limiting device 330 is typically located closer to the electrode output while the power limiting device 300 is more isolated from the electrode output. The additional amount of isolation circuitry introduces a lag time into the responsiveness of the power limiting device. Thus, one device reacts slower and while the device closer to the electrode reacts faster. In one embodiment, there is about a 200 ms delay in order for the current to reach the power limiting device 300.

As an example of how the devices would function together, when an attached RF probe touches a metallic object such as a cannula or screw in the surgical site, the spark limiting device 330 activates to reduce the current output from the power supply to zero. The current output may be reduced to some nonzero value so long as sparks are not generated. The spark limiting device 330 introduces a delay and then checks to see if it can power up. During this time, the power limiting device 300 also continues to check about every duty cycle to see if power should be increased. In one embodiment, the power limiting device 300 introduces more delay into the system since its duty cycle is longer than the 2–90 ms delay of the spark limiting device. As soon as the probe is removed from the extremely low impedance site and current drawdown stays within acceptable ranges, the probe resumes normal operations. Which ever device has the tail end of the delay will control when power is returned to the probe. If the probe is close to target tissue, it will preferably automatically resume operation at the setting prior to the spark limiting mode. If the probe is no longer in contact with target tissue, then the probe will most likely be in pulsatile mode while awaiting to be repositioned.

C. Fluid Interlock

Figure 15:
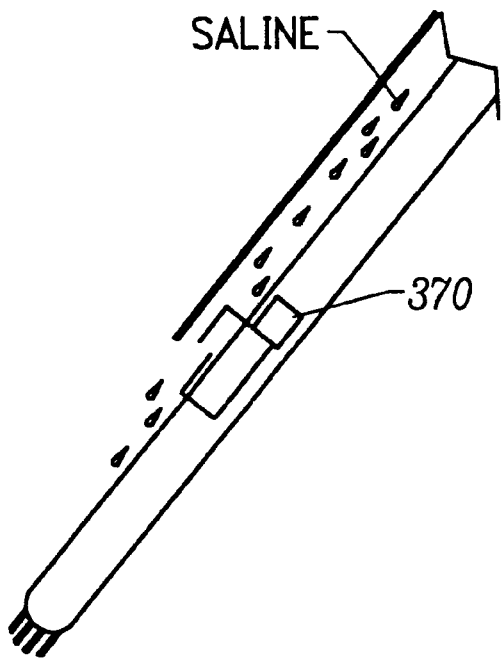
FIGS. 15–17 illustrate embodiments of a flow interlock mechanism according to the present invention.

Referring to FIG. 15, the power supply 28 may include a flow interlock device 370 which prevents activation of output from the power supply unless conductive or isotonic fluid is present at the working end of an attached RF probe. For devices using cold ablation techniques with power supply 28, undesired tissue damage may occur if conductive fluid is not present between the active electrode and the tissue, or between the active and return electrodes in bipolar embodiments. Additionally, the accidental discharge of radio frequency (RF) current into sensitive tissue such as cardiac tissue without isotonic fluid present may cause other more serious problems. For example in cardiac tissue, disrupting cardiac tissue contraction through passage of current through the heart can defibrillate the patient's heart causing uncontrolled, ineffective contractions.

In one embodiment, the device 370 detects that isotonic fluid is present between an active electrode and a return electrode on the attached RF probe. In a preferred embodiment, the flow interlock device 370 relies on the electric conductivity of the isotonic fluid to determine if isotonic fluid is flowing or present near the active end of the probe. The fluid to be detected may be a saline solution injected into the surgical area by the electrosurgical system, or alternatively, the fluid may be some naturally occurring fluid such as blood or other body fluid that has electrolytic qualities sufficient for cold ablation surgery. It should be understood that the device 370 may also be adapted for use with a monopolar RF probe that does not have a return electrode. In a monopolar embodiment, the device 370 would preferably detect for isotonic fluid near the active electrode.

Figure 16:
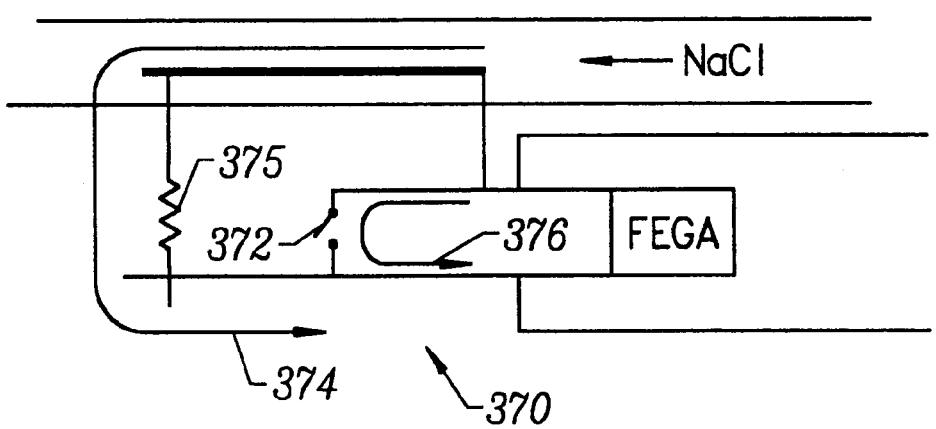

In a preferred embodiment (FIG. 16), the interlock device 370 uses a conductive fluid sensor such as switch 372 which creates an open circuit when isotonic fluid is present and a closed circuit when fluid is not. When fluid is present, the switch creates an open circuit and forces current to flow in a first electrical pathway 374 having a resistor 375 of a known resistance value. When fluid is not present, switch 372 is closed and creates a second electrical path 376 which short circuits the first pathway 374. Both pathways are connected to a controller device such. as an FPGA. The sensor switch 372 provides such a distinct change in resistance that the presence of fluid is easily registered by the device 370. By detecting the change in resistance, an attached logic circuit such as the FPGA can determine if it is safe to supply power to the RF instrument. Without the flow of isotonic fluid along the probe or presence of fluid at the active end of probe, output current from the RF probe would not travel to the return electrode along a desired pathway, instead passing through low impedance pathways in the patient's body. This interlock device 370 prevents such accidental power output which is particularly useful in environments sensitive to stray electric currents such as the heart.

Figure 17:
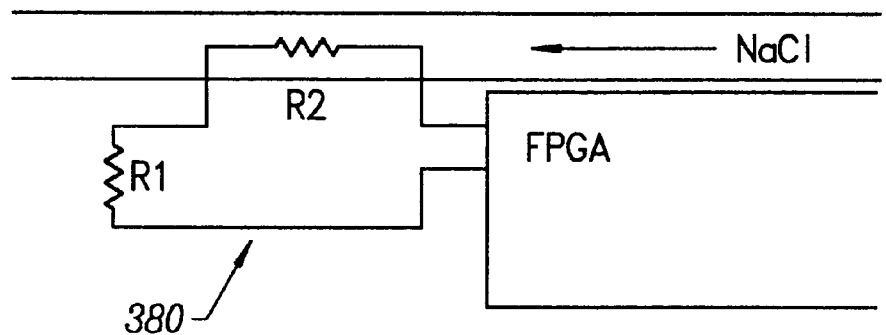
Figure 19:
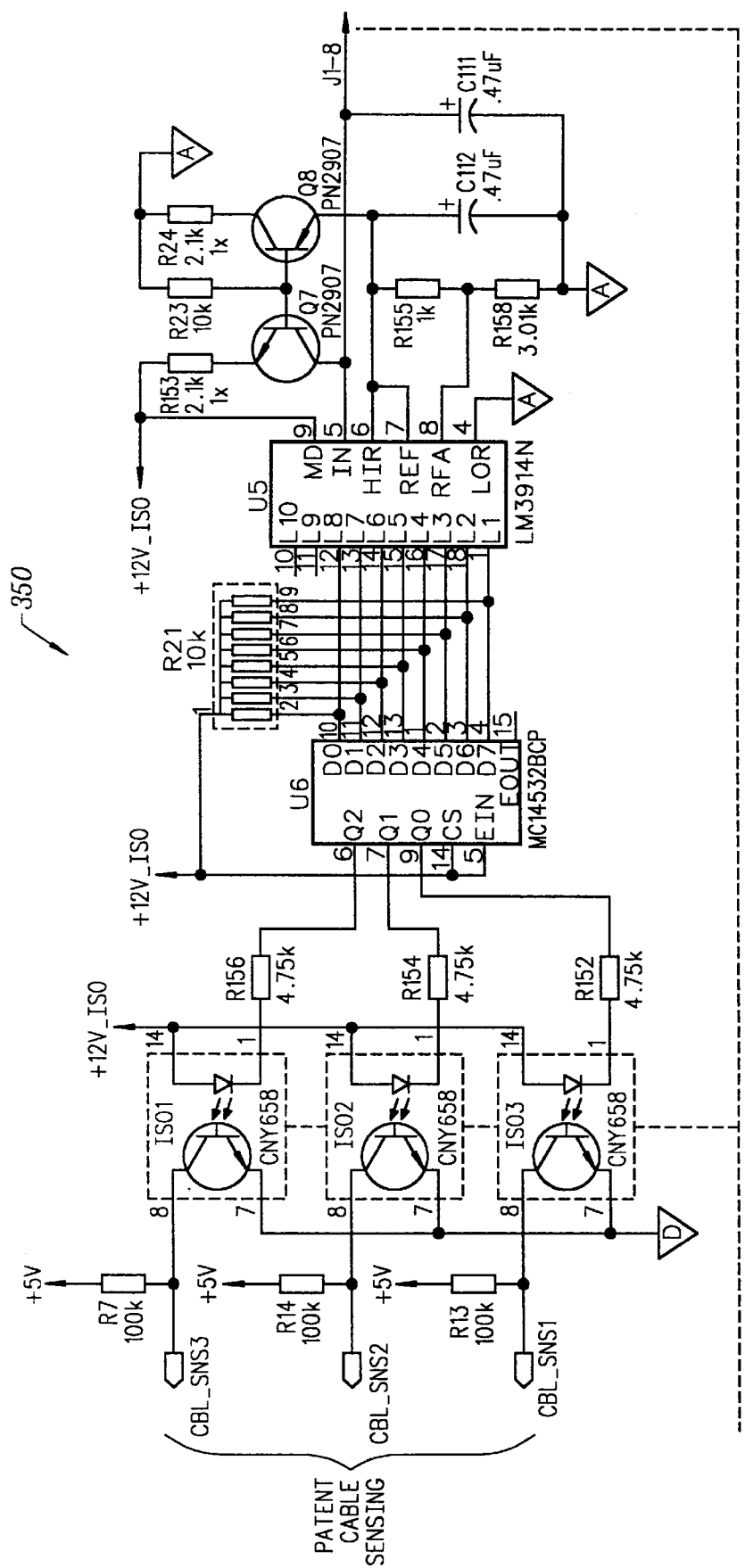

In an alternative embodiment (FIG. 17), the interlock device 380 uses at least two resistors 382 and 384 having values R1 and R2. The resistor 384 is located in the fluid flow path. If there is fluid present in the flow path, the resistor value R2 of resistor 384 will vary due to the conductivity of the fluid. The change will be sufficient for detection by U5, U6 and photo-isolator of the power supply 28 (FIG. 19). These signals are fed to FPGA for processing. The FPGA is programmed to recognize the presence of the fluid flow and allows power output if there is fluid. If it detects the absence of the fluid, it will also give a warning sound or a warning light. The display on the power supply 28 will show 0 power as well. When fluid is turned on again, the FPGA will remember the previous setting and enable the power output.

D. Identification

Figure 18:
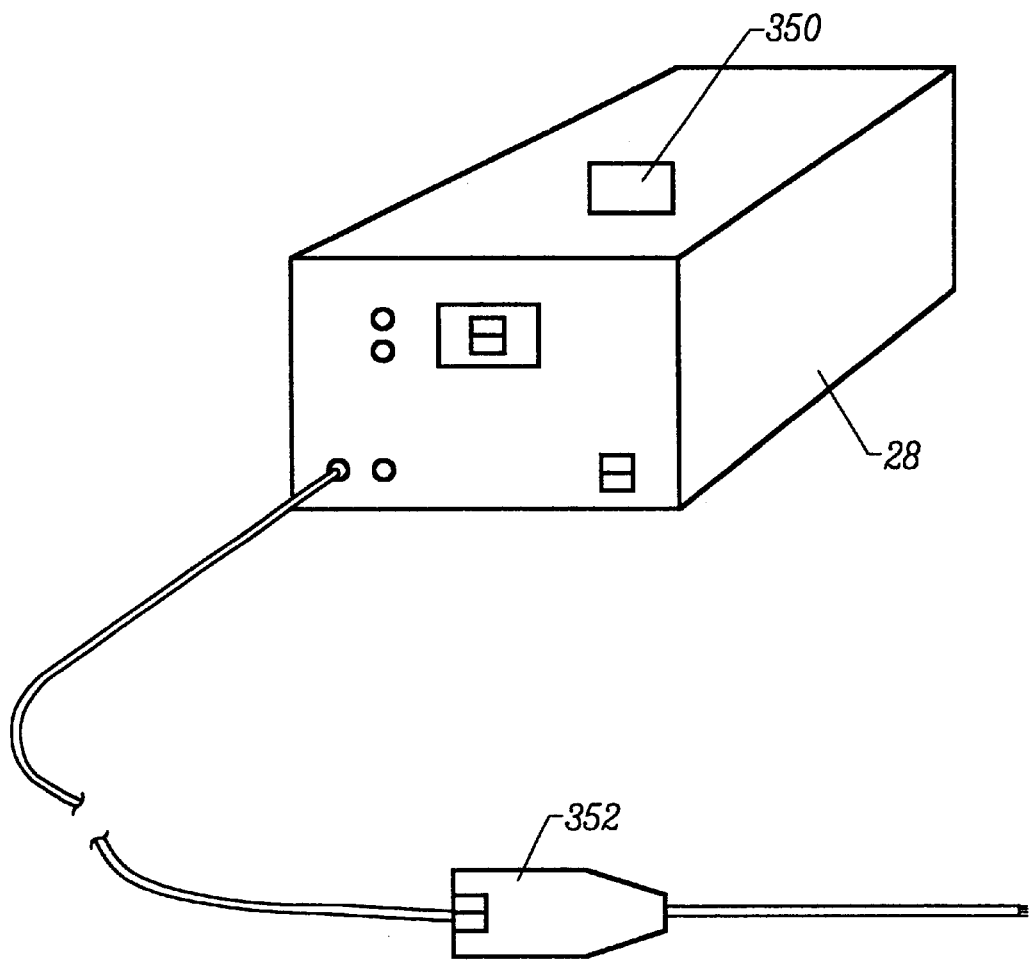
FIGS. 18–19 are an overview and a schematic of a probe identification mechanism according to the present invention.

Referring now to FIG. 18, in preferred embodiments, the power supply 28 is used with a variety of different surgical probes and instruments. To prevent accidental overpower and to maximize convenience for the user, the power supply 28 may include a probe or attachment identification device 350 which identifies the attached probe and automatically sets variables such as the maximum power output acceptable by the attached probe. The identification device 350 is designed for use with coding resistors in electrosurgical probes to limit the amount of voltage applied to the probe according to its design limits. In general terms, the design limits are revealed by the internal coding resistor, which is typically contained in the handle portion of the disposable probe. This feature allows the power supply to be used with a wide variety of probes and in a wide variety of surgical procedures. In addition, this sensing capability can be used to detect whether electrically conductive fluid is present adjacent the electrode terminals to prevent energizing the probe if the appropriate amount of fluid is not present. The generator may also include a voltage threshold detector for setting peak RF output voltage limits.

In one embodiment, each probe has a built in resistor 352. The identification device identifies the probe based on the resistor value associated with each probe. In the representative embodiment, the device 350 responds to six different resistor values of 200, 412, 576, 750, 909, and 1070 ohms. Specifically, there are six different resistor values plus open circuit mode and short circuit mode. Although not limited in this manner, the particular resistor values recited typically correspond to differing levels of ablation intensity.

Referring to FIG. 19, the identification device 350 embodied as the sensing circuit 360 detects and determines the resistor value in the RF probe. The circuit 360 uses analog input from one of six different resistor values plus short and open circuits to determine eight different voltage ranges. The analog voltage is sensed by U5 which is a Dot/Bar display drive. U5 then outputs digital signals to U6 which is a 8 bit priority encoder. U5 outputs a 3 bit digital signal and these 3 bits give us 8 different states. Each of these three bits is driving an opto-isolator such as ISO1, ISO2 and ISO3. The three outputs from the opto-isolators are fed into a FPGA which is programmed to recognize these 3 bits of information (or 8 states). Of course, it is recognized that more probes can be recognized by using a display drive having more bits. Advantageously, however, the present embodiment of the identification device 350 provides certain cost efficiencies and robustness associated with using relatively simple, inexpensive components.

E. Mode Switching

Referring back to FIG. 2, the power supply of the present invention can provide power to an RF probe over a variety of power ranges and provide different therapeutic affects. In an ablation mode, a sufficient voltage is applied to the electrode terminals to establish the requisite conditions for molecular dissociation of the tissue (i.e., vaporizing a portion of the electrically conductive fluid, ionizing charged particles within the vapor layer and accelerating these charged particles against the tissue). The requisite voltage level for ablation will vary depending on the number, size, shape and spacing of the electrodes, the distal the electrodes extend from the support member, etc.

In the subablation mode, the power supply 28 applies a low enough voltage to the electrode terminals (or the coagulation electrode) to avoid vaporization of the electrically conductive fluid and subsequent molecular dissociation of the tissue. In an exemplary embodiment, the surgeon may automatically toggle the power supply between the ablation and coagulation modes by alternatively stepping on foot pedals 24, 25, respectively. This allows the surgeon to quickly move between a subablation and ablation in situ, without having to remove his/her concentration from the surgical field or without having to request an assistant to switch the power supply. By way of example, as the surgeon is sculpting soft tissue in the ablation mode, the probe will typically simultaneously seal and/or coagulation small severed vessels within the tissue. However, larger vessels, or vessels with high fluid pressures (e.g., arterial vessels) may not be sealed in the ablation mode. Accordingly, the surgeon can simply step on foot pedal 25, automatically lowering the voltage level below the threshold level for ablation, and apply sufficient pressure onto the severed vessel for a sufficient period of time to seal and/or coagulate the vessel. After this is completed, the surgeon may quickly move back into the ablation mode by stepping on foot pedal 24.

Subablation also encompasses operating the probe to shrink or contract tissue at a target site. In collagen shrinkage procedures, the RF energy heats the tissue directly by virtue of the electrical current flow therethrough, and/or indirectly through the exposure of the tissue to fluid heated by RF energy, to elevate the tissue temperature from normal body temperatures (e.g., 37° C.) to temperatures in the range of 45° C. to 90° C., preferably in the range from about 60° C. to 70° C. Thermal shrinkage of collagen fibers occurs within a small temperature range which, for mammalian collagen is in the range from 60° C. to 70° C. A more complete description of this modality can be found in commonly assigned U.S. patent application Ser. No. 08/942,580, filed Oct. 10, 1997, the complete disclosure of which is incorporated herein by reference for all purposes.

The system preferably includes three foot pedals which allows the surgeon to automatically switch between the coagulation and ablation modes, and to select the voltage level in the ablation mode. In an exemplary embodiment, the power supply 10 has an operator controllable voltage level adjustment 38 to change the applied voltage level, which is observable at a voltage level display 40. Power supply 10 also includes first, second and third foot pedals 24, 25, 26 and a cable 26 which is removably coupled to a receptacle 30 with a cable connector 28. Although applicant has found that foot pedals are convenient methods of controlling the power supply while manipulating the probe during a surgical procedure, it will be recognized that the voltage and modality of the power supply may be controlled by other input devices such as buttons located on the handle of the RF probe. The foot pedals 24, 25, 26 allow the surgeon to remotely adjusting the energy level applied to electrode terminals 104. In an exemplary embodiment, first foot pedal 24 is used to place the power supply into the "ablation" mode and second foot pedal 25 places power supply 10 into a subablation mode such as a "coagulation" mode. The third foot pedal 26 allows the user to adjust the voltage level within the "ablation" mode. Once the surgeon places the power supply in the "ablation" mode, voltage level adjustment 38 or third foot pedal 26 may be used to adjust the voltage level to adjust the degree of aggressiveness of the ablation.

In the preferred embodiment, the voltage is toggled between the coagulation and ablation modes by adjusting the output voltage or amplitude of the oscillating current signal. Thus, the shape of the waveform and the frequency of the signal remain substantially fixed in both modes (and as the voltage is being adjusted in the ablation mode). This design minimizes the interference that may otherwise be caused by frequent adjustment of the waveform and/or frequency of the output signal. This coagulation mode lowers voltage without which changing wave forms of the output.

When the coagulation mode foot pedal is depressed, a signal is sent to the FPGA which will lower output to a fixed voltage between about 50–65 volts which is not enough to cause ablation but creates sufficient heat for coagulation. When the foot pedal is released, the previous power setting for ablation (which is memorized) will come back. This coagulation circuit preferably outputs a square wave typically at least about 100 kHz, similar that used in the ablation mode.

F. Zero Switching

Figure 20:
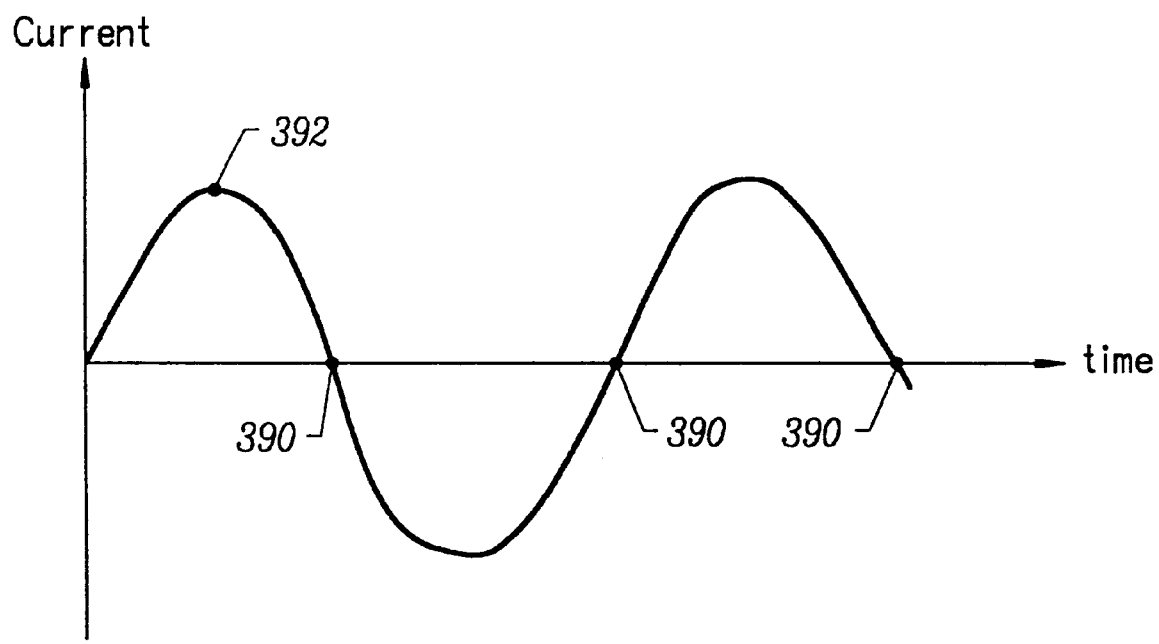
FIG. 20 is graph of alternating current and zero voltage positions of an exemplary power supply according to the present invention.

Referring to FIG. 20, in an exemplary embodiment, the power supply 28 includes a switching power supply to increase the peak power output of the generator. FIG. 20 shows a sinusoidal wave form with points 390 denoting the zero voltage positions where the power supply activates and deactivates. This minimizes the noise output which occurs when power is activated over its duty cycle. Activating the power at the maximum amplitude position 392 creates the greatest amount of electronic noise. The zero voltage switching topology minimizes the electromagnetic noise output of the power supply during surgical procedures, thereby ensuring that US and foreign EMI requirements are met. The switching power supply has circuitry which only allows the supply to activate on the zero voltage position of a sinusoidal wave form of AC current.

Specifically, the power circuit 500 (FIGS. 9 and 14) is designed to meet the leakage current and EMC standard required by UL and IEC601. In conventional circuit design, low EMC usually at the expense of high leakage current. The zero voltage switching applied in the controller reduces EMI substantially so that leakage current does not have to be increased. The DC/DC converter includes Q1, Q2, Q3, Q4, T2, and U2 etc. which makes up the circuit so that it switches at zero voltage. The DC/AC converter includes Q9, Q10, Q12, Q13, T10, and U31 etc. which makes up the circuit so that it switches at zero voltage. The power circuit has a full-wave bridge configuration and four switching elements. It is capable, through the antiparallel diodes within the MOSFETs, of four-quadrant operation, returning reactive load energy to the power supply for self-protection. The inverter runs at a fixed 50% duty cycle whenever drive (of about 100 kHz or other) from the FPGA is available. The inverter is running at zero voltage switching mode to reduce EMI and indirectly reduces leakage current.

III. Applications

Figure 21:
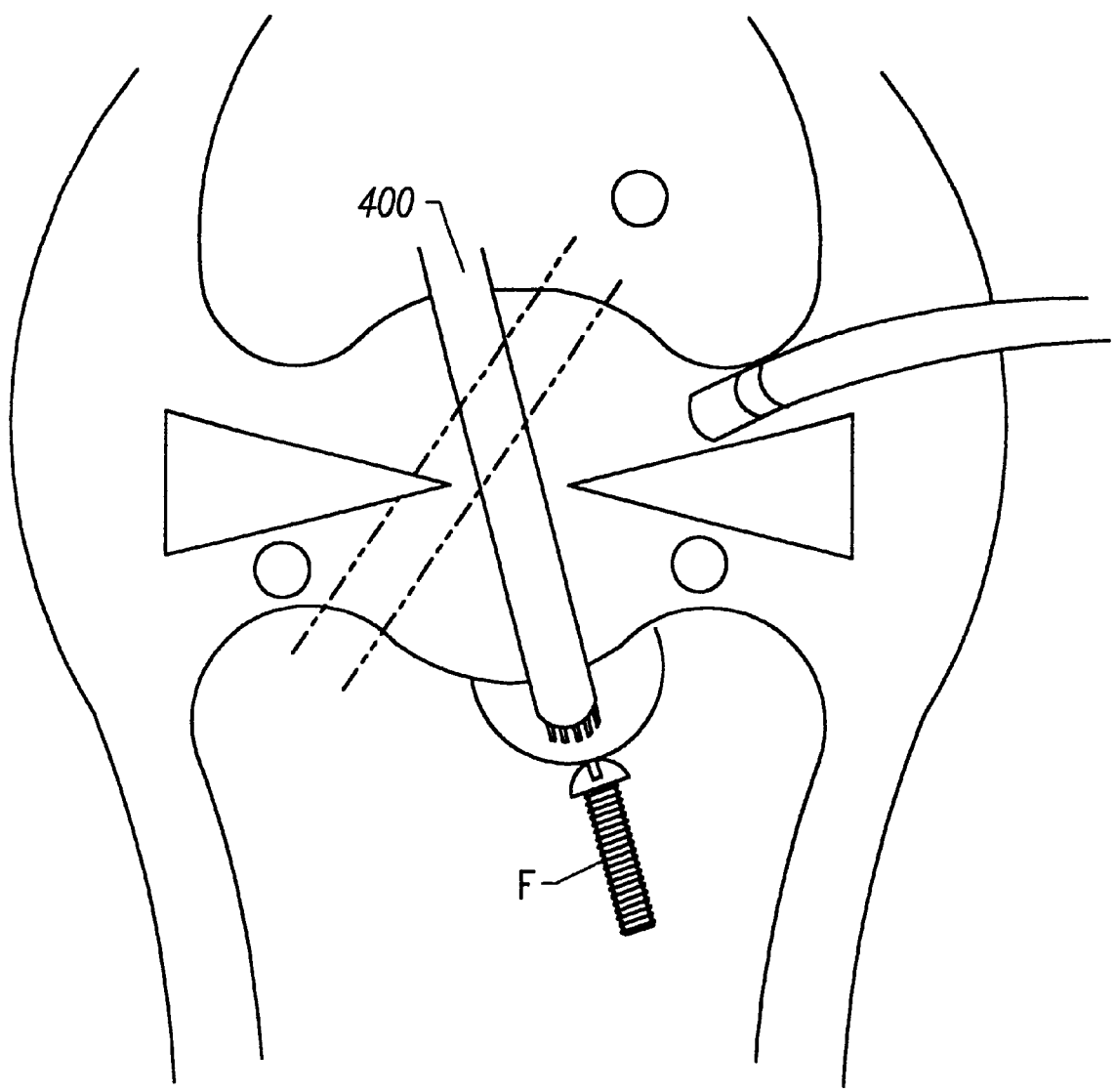
FIG. 21 illustrates a method of applying high frequency electrical energy tissue in a joint according to the present invention.

Although not limited in this manner, the present invention finds particular use in arthroscopic procedures. Referring to FIG. 21, the power limited and spark limited mechanisms on a power supply of the present invention allows a surgeon to clean body tissue covering fasteners or screws F used to attach ligaments from the femur to the tibia or other bone structure. With the present invention, the soft tissue may be removed right up to the metallic material of the fastener with minimal risk of sparking or undesired tissue necrosis resulting from the sparking.

In arthroscopic surgical procedures for knee reconstructive surgery, metallic fastener devices are used to engage and endosteally mount a bone end of a bone tendon, bone or other type of ligament graft in position in the ligament tunnel. It is desired in some cases to intersect a prepared femoral or tibial tunnel section of a straight ligament tunnel and for fitting and guiding a fastener device, such as a set screw, interference screw or cross pin therethrough to engage and mount an end of a ligament graft in the tunnel section. A ligament anchor may be used to repair the knee cruciate ligament. In an arthroscopic cruciate ligament replacement surgical procedure, the ligament graft end is endosteally secured in the femur endosteum by drilling from within the knee intra-articular joint to the femoral tunnel and fitting a set screw, or the like fastener in the ligament graft seated therein.

In some cases, unfortunately, anchor replacement procedures are necessary to replace defective anchors or to reattach the ligament to the bone. To access the metal anchor, soft tissue needs to be removed right up to the anchor or fastener F. Performing such a procedure with an electrosurgical probe requires removing the tissue without delivering current into the anchor. Thus, an RF probe 400 connected to a power supply 28 of the present invention will remove tissue and stop current output when the probe contacts the metal anchor.

The power supply 28 of the present invention is also of particular use in other arthroscopic procedures such as meniscus repair which operate in a confined environment. The meniscus is a crescent-shaped disk positioned in the knee and attached to the joint capsule and serves as a buffer between the bones of the femur and the bones of the tibia and fibula. Surgical repair of the meniscus is generally performed arthroscopically and requires precision instruments to perform the procedure in a confined area so that damage to the surrounding tissue and muscle is limited. During these procedures, the surgeon may accidentally contact the electrosurgical probe with metallic objects, such as an endoscope or cannula, in a confined area like the synovial sac of the knee. The low impedance of a metallic cannula or the shaft of an endoscope, as compared to the impedance of the surrounding body tissue, may cause a spark or excessive pulse/power drawdown from the RF probe. The spark may cause undesired tissue necrosis and also permanently damage other surgical equipment such as the endoscope. The power supply 28 will prevent such sparking by stopping current output before the spark can form.

Although the foregoing invention has been described in detail for purposes of clarity of understanding, it will be obvious that certain modifications may be practiced within the scope of the appended claims. For example, the power supply may be coupled to probes or catheters of designs other than those disclosed in the present application. The power supply and associated probes may also be used in a variety of other surgical procedures as described above.

What is claimed is:

1. A method for applying electrical energy to a target site on or within a patient's body, the method comprising:
   introducing an electrically conductive fluid to a target site on or with a patient's body;
   positioning an electrode terminal within the electrically conductive fluid in contact with or close proximity to tissue at the target site on or within a patient's body, the electrode terminal being coupled to a high frequency power supply;
   positioning a return electrode within the electrically conductive fluid such that the return electrode is not in contact with the tissue;
   applying high frequency voltage to the electrode terminal to at least modify the tissue; and
   detecting the current output from the power supply; and
   reducing power applied to the electrode terminal when the current output exceeds a predetermined threshold current.

2. The method of claim 1 further comprising interrupting current output when the electrode terminal is brought adjacent to a metal object within the patient's body and introducing a predetermined delay after power is disrupted.

3. The method of claim 1 wherein the detecting step further comprises:
   conditioning a signal from a current sensor; and
   comparing a value of said signal to a value of a predetermined threshold current.

4. A method of claim 1 wherein the predetermined threshold current is about 1.0 to 3.0 amperes for spark limiting.

5. A method of claim 1 further comprising positioning the electrode terminal within the synovial sac of the knee to remove soft tissue.

6. A method of claim 1 further comprising passing the electrode terminal through the synovial sac of the knee to remove soft tissue around a fastener.

* * * * *